(12) United States Patent
Lavi et al.

(10) Patent No.: US 7,530,964 B2
(45) Date of Patent: May 12, 2009

(54) NEEDLE DEVICE AND METHOD THEREOF

(75) Inventors: Gilad Lavi, Rishon Lezion (IL); Gil Yigal, Gan-Yavne (IL); David Daily, Herzliya (IL); Udi Carmel, Ganey Tikva (IL); Avi Azoulay, Ashdod (IL); Oz Cabiri, Macabim (IL)

(73) Assignee: Elan Pharma International Limited, Athlone (IE)

( * ) Notice: Subject to any disclaimer, the term of this patent is extended or adjusted under 35 U.S.C. 154(b) by 838 days.

(21) Appl. No.: 09/883,025

(22) Filed: Jun. 17, 2001

(65) Prior Publication Data

US 2002/0055711 A1     May 9, 2002

Related U.S. Application Data

(60) Provisional application No. 60/215,770, filed on Jun. 30, 2000.

(51) Int. Cl.
    *A61M 5/00*     (2006.01)
(52) U.S. Cl. ....................................................... 604/110
(58) Field of Classification Search ................ 604/110, 604/116, 117, 272, 136–137, 141, 181, 187, 604/156, 157, 198, 197, 192, 130–131, 134, 604/890.1; 128/919
    See application file for complete search history.

(56) References Cited

U.S. PATENT DOCUMENTS

| | | | | |
|---|---|---|---|---|
| 3,430,626 | A | * | 3/1969 | Bergman ..................... 604/137 |
| 4,487,602 | A | * | 12/1984 | Christensen et al. ......... 604/137 |
| 4,894,054 | A | * | 1/1990 | Miskinyar .................... 604/136 |
| 5,147,303 | A | * | 9/1992 | Martin ......................... 604/110 |
| 5,201,716 | A | * | 4/1993 | Richard ....................... 604/187 |
| 5,267,963 | A | * | 12/1993 | Bachynsky .................. 604/134 |
| 5,279,582 | A | * | 1/1994 | Davison et al. .............. 604/198 |
| 5,312,364 | A | | 5/1994 | Jacobs |
| 5,364,370 | A | * | 11/1994 | Szerlip et al. ................ 604/192 |
| 6,149,626 | A | * | 11/2000 | Bachynsky et al. .......... 604/134 |
| 6,238,375 | B1 | | 5/2001 | Powell |

FOREIGN PATENT DOCUMENTS

| | | |
|---|---|---|
| EP | 0 709 104 | 10/1995 |
| EP | 0 753 317 | 1/1997 |
| FR | 2 686 022 | 1/1992 |

(Continued)

OTHER PUBLICATIONS

International Search Report, PCT/GB01/02921—Jan. 25, 2002.

*Primary Examiner*—Nicholas D Lucchesi
*Assistant Examiner*—Theodore J Stigell
(74) *Attorney, Agent, or Firm*—Fox Rothschild LLP

(57) ABSTRACT

A needle device has a needle retraction mechanism that retracts the needle upon removing the device from the skin surface (either intentionally or unintentionally). Once the needle is retracted, the device is rendered inoperative. The needle can be further made inoperative by bending it when one attempts to reuse the device. In another embodiment, a needle opening formed in the base of the housing can be covered to render the needle inoperative when one attempts to reuse the device. In another embodiment, the needle device instead has a needle shield that automatically covers the needle after use.

19 Claims, 30 Drawing Sheets

FOREIGN PATENT DOCUMENTS

| WO | WO 93/01851 | | 2/1993 |
| WO | WO 9301851 A1 | * | 2/1993 |
| WO | WO 98/57683 | | 12/1998 |
| WO | WO 99/22790 | * | 5/1999 |
| WO | WO 99/52509 | | 10/1999 |
| WO | WO 99/62576 | | 12/1999 |

* cited by examiner

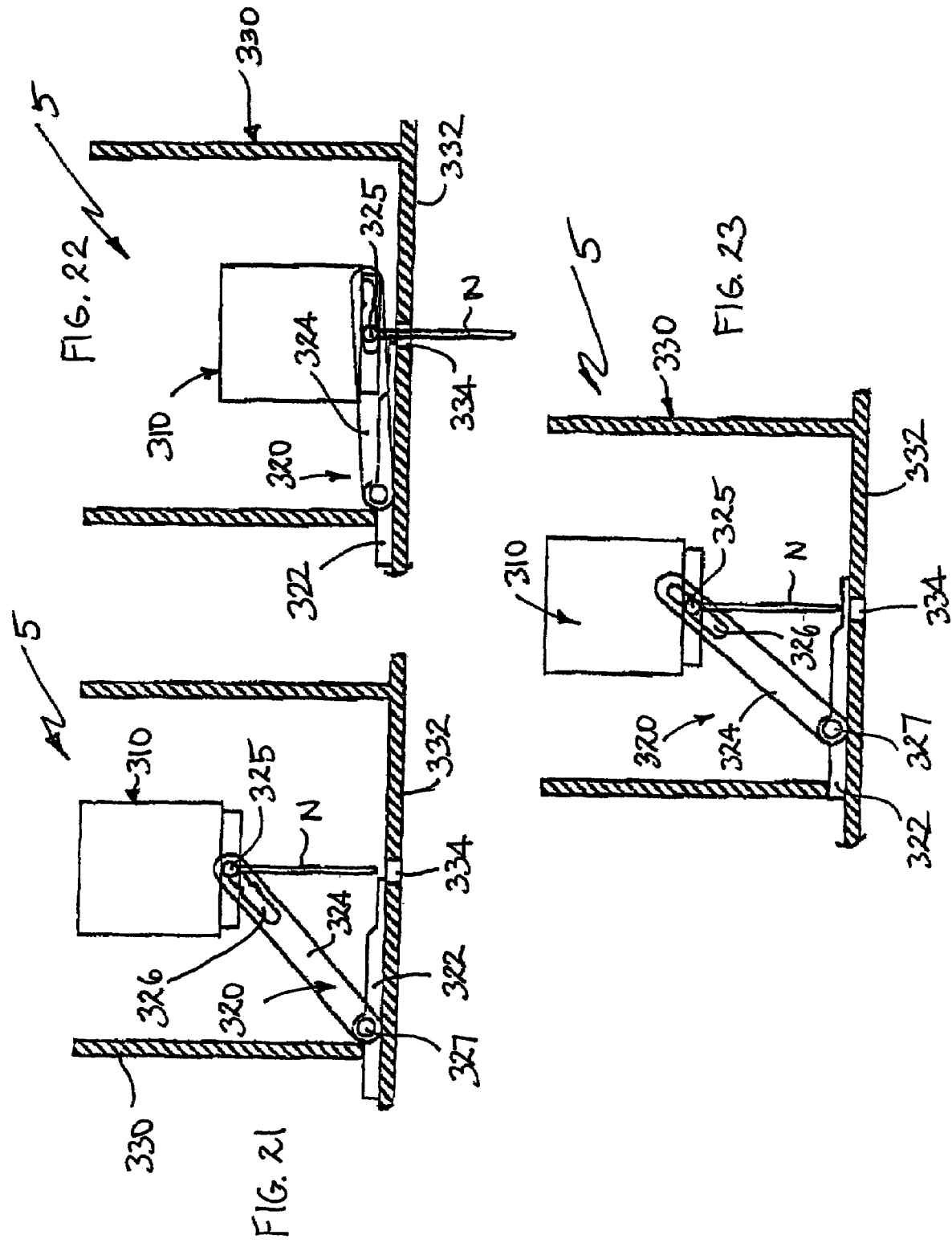

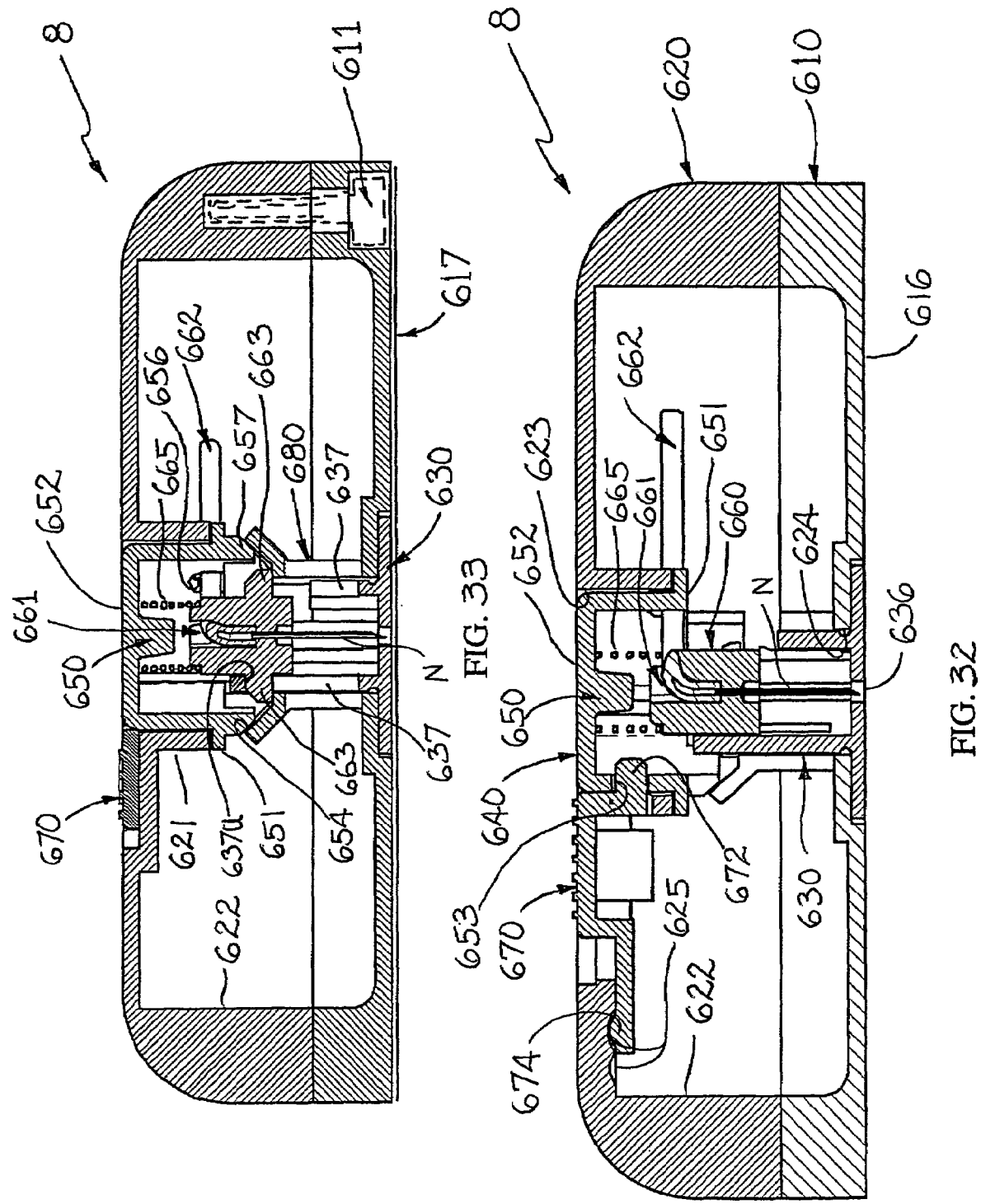

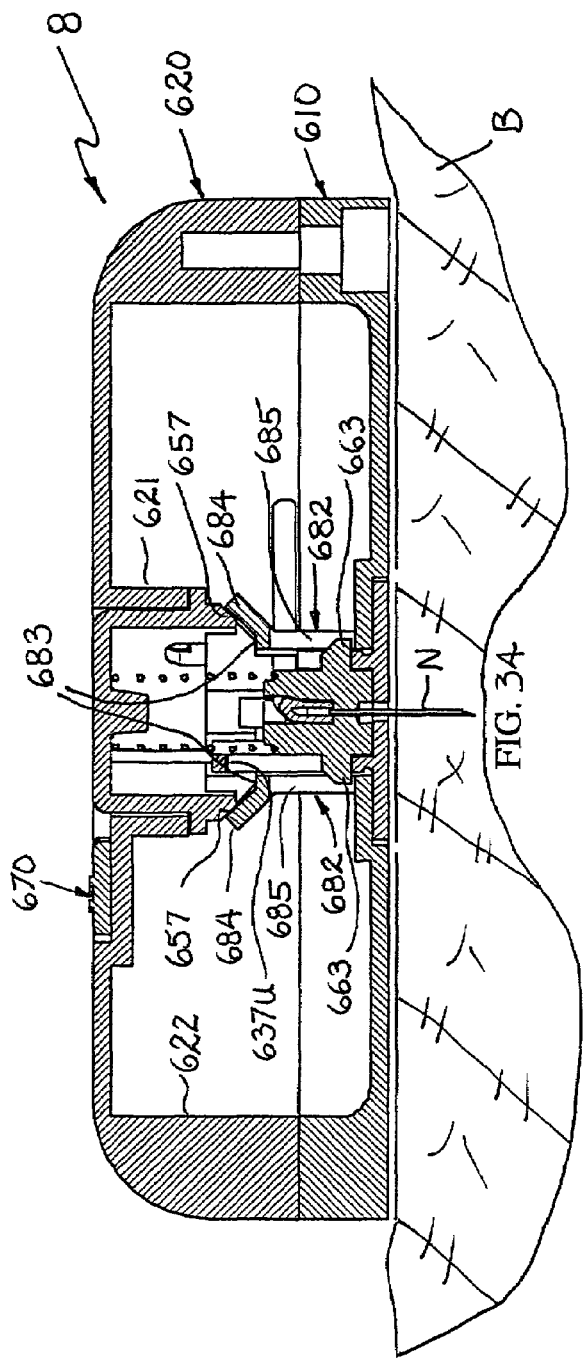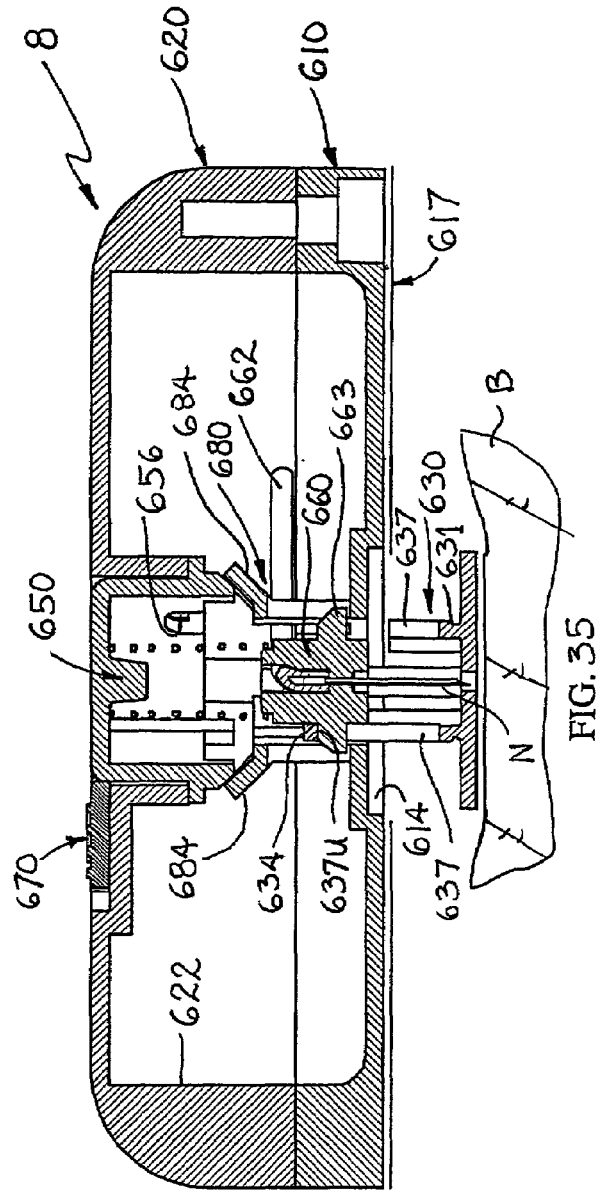

NEEDLE DEVICE AND METHOD THEREOF

BACKGROUND

Penetrating instruments or needles are widely used in medical procedures to gain access to anatomical cavities ranging in size from the abdomen to small blood vessels, such as veins and arteries. Such penetrating instruments include a sharp tip or point to pierce the tissue forming a cavity wall. Once the penetrating member has been removed from the tissue, the penetrating member becomes exposed to the user or operator. An inadvertent prick after the needle is exposed to the patient's blood or body fluids can be dangerous. The transmission of pathogens from an inadvertent prick could lead to infection and diseases transmitted through the bloodstream, such as hepatitis and AIDS. Such infections may result in serious illness or even death.

A number of design approaches have been developed to prevent "needle stick" injuries. One type of device, categorized as a sliding sheath design, uses a physical barrier positioned about the needle after use. A second type of device withdraws the needle tip into a housing after use. These devices use a spring to push or pull the needle into the housing when the user activates it. But in some instances where a manual activation is required, the user may forget or simply fail to activate the needle withdrawal device. In that case, the needle is left exposed, presenting a risk to the user or caregiver.

Thus, there is a need to provide an automatic needle retraction system, one that does not require user activation, to minimize the potential risk of "needle stick" and the risk of infection and potential death associated therewith. The present invention addresses this need.

SUMMARY

The present invention relates to a needle device and a method thereof. According to one aspect of the present invention, the needle device has an automatic needle retraction device. According to another aspect, the needle device has an automatic needle-enveloping device.

The needle device according to the present invention can include a housing, a needle, an actuator, and a retraction mechanism. The housing can have a base for placement against a surface of a needle-penetrating site. The base can include a first opening for passage of the needle, which is mounted for a movement between a retracted position in the housing and an extended position. A portion of the needle extends through the first opening in the extended position. The actuator is movably mounted to the housing and movable between an unactuated position in which the needle is in the retracted position and an actuated position in which the needle is in the extended position. The needle can be biased toward the retracted position.

According to one aspect of the invention, the retraction mechanism can move the needle to the retracted position upon releasing the base from the site surface. The retraction mechanism can also maintain the needle in the extended position upon moving the actuator to the actuated position.

The housing can include an actuator guide that guides the actuator through a predetermined path of movement. The guide can comprise a substantially U-shaped channel formed in the housing. The U-shaped channel comprises a first substantially vertical guide portion, a second substantially vertical guide portion, and a horizontal guide portion connecting lower ends of the first and second vertical portions. The actuator guide can further include a lock portion contiguous with the second vertical guide portion. The actuator can be rotatably and vertically movably mounted to the housing, and can further include a pin adapted to be guided in the U-shaped channel.

A spring can bias the actuator to the unactuated position. The spring can have one end thereof fixedly mounted to the actuator and another end thereof fixedly mounted to the base to enable creation of a spring torsional load when the actuator is rotated relative to the base. The spring can be torsionally preloaded to rotate the actuator from the first vertical guide portion to the second vertical guide portion through the horizontal guide portion upon moving the actuator to the actuated position. The first and second vertical guide portions can be angled from the vertical so that moving the actuator to the actuated position torsionally loads the spring and biases the actuator to rotate to the second vertical guide portions through the horizontal guide portion. The spring torsional preloading can further rotate the actuator into the lock portion to lock the actuator from moving to the actuated position. The angled second vertical guide portion torsionally loads the spring as the pin is guided in the angled second vertical guide portion while the actuator is being moved to the unactuated position, and rotates the actuator into the lock portion as the torsional load is released, locking the actuator from moving to the actuated position.

The retraction mechanism can include a trigger member movably or pivotally mounted to the housing. The trigger member can have a first portion that can engage the actuator and a second portion that can contact the site surface. The first portion thereof can engage the pin and prevent the actuator from moving to the unactuated position when the pin is positioned in the second vertical guide portion and the second portion thereof is contacting the site surface. The base can include a second opening through which the second portion of the trigger member can contact the site surface.

The actuator can comprise a depression member movably mounted to the housing and a needle holder movably mounted relative to the depression member, the depression member being movable relative to the needle holder. The retraction mechanism can include at least one trigger member movably mounted to the housing. The trigger member can have a first portion that can maintain the needle holder in position so that the needle is maintained in the extended position, and a second portion that can contact the site surface. The trigger member can be biased to extend outwardly from the base.

The device can include first and second locks. The first lock can lock the depression member relative to the housing upon the actuator being moved to the actuated position. The second lock can engage the needle holder. The second portion of the trigger member can engage the second lock to maintain the needle in the extended position when the second portion of the trigger member is contacting the site surface. The second lock can comprise a plurality of projections insertable through the depression member.

The device can include a needle bending assembly that plastically bends the needle to misalign the needle from extending through the first opening. The needle bending assembly can comprise a cam that plastically bends the needle out of alignment with the first opening. The cam can be integrally formed with the base and contiguous with the first opening. In this respect, the actuator can be rotatably mounted to the housing. The needle N can be pre-bent at an acute angle and the bent needle can ride on the cam to plastically deform the needle to about 90°.

According to another aspect of the invention, the retraction mechanism can automatically move the needle from the extended position to the retracted position and prevent the needle from moving back to the extended position once the needle has been moved from the extended position to the retracted position.

The retraction mechanism can include a cover member for covering the first opening after the needle moves from the extended position to the retracted position. The retraction mechanism can include at least one linkage pivotally connected to the actuator and pivotally connected the cover member. In another embodiment, the linkage is pivotally connected to the actuator and has a free end. Moving the actuator from the actuated position to the unactuated position can move the cover member and cover the first opening.

The linkage can have an axially extending slot having a first end and a second end, and a pivot pin connected to the actuator and guided in the slot. The pin can be positioned in the first end when the actuator is in the unactuated position, and the pivot pin can move toward the second end as the actuator is moved to the actuated position. The device can further include means for decreasing the effective length of the slot after the pivot pin is moved toward the second end.

The means for decreasing the effective length of the slot can comprise a detent that creates a slot width dimensioned smaller than the pin. A manual actuating force for moving the actuator to the actuated position can be sufficient to force the pin past the detent, but the biasing force of the actuator toward the unactuated position is made insufficient for the pin to clear the detent, but sufficient to move the cover member to make up for the slot length decrease.

In another aspect of the invention, in the alternative embodiment where the linkage has a freely movable end, the means for decreasing the effective length of the slot also comprises a detent that creates a slot width dimensioned smaller than the pin. A manual actuating force for moving the actuator to the actuated position can be sufficient to force the pin past the detent, but the biasing force of the actuator toward the unactuated position is insufficient for the pin to clear the detent, but sufficient to shift the linkage to make up for the slot length decrease.

The device can include, instead of the cover member, a needle bending mechanism for bending the needle upon moving the actuator to the actuated position after the actuator is moved from the actuated position to the unactuated position. The needle bending mechanism can be a cam formed adjacent to the slot and positioned to engage the needle and apply a bending moment that moves the needle to misalign with the first opening in the base.

In another aspect of the invention, the needle device can comprise a housing having a base with an opening, a needle, and an actuator, and a needle shield. The base with an opening is adapted to engage the site surface. The needle can be mounted for a movement between a retracted position in the housing and an extended position, where a portion of the needle extends through the first through hole. The actuator is movably mounted to the housing for moving the needle to the extended position. The needle shield is movably mounted relative to the housing between a retracted position and an extended position. The needle shield is configured to move to the extended position upon removing the base from the site surface.

According to one aspect, the needle shield is biased toward the extended position and is released to the extended position upon the needle being moved to the extended position and the base being released from the site surface.

According to another aspect, the base has an adhesive layer for adhering the device the site surface. A portion of the adhesive layer is attached to a lower end of the needle shield. The needle shield is freely movable toward the extended position when the needle is moved to the extended position so that the adhesive layer portion adhered to the lower end of the needle shield and the site surface applies a pulling force as the base is removed from the skin site to automatically cover the needle. The actuator can further include a depression member and a needle holder movably mounted relative to the depression member. The needle holder holds the needle. The needle holder can be biased to move the needle to the extended position. Thus, the needle can be biased toward the extended position. The device can further include a lock member that can engage the needle holder to maintain the needle in the retracted position, and a spring that can bias the needle toward the extended position. The depression member can unlock the lock member to allow the spring to propel the needle holder and the needle to the needle extended position. The device can also include a safety tab movable between a lock position and an unlock position to lock the depression member.

A method of retracting a needle of a needle device can comprise: attaching the housing to the surface site; providing the needle mounted for a movement between a retracted position in the housing and an extended position, where a portion of the needle extends through the opening formed in the base; pushing the needle to the extended position and into the surface of the site; locking the needle in the extended position; and releasing the needle into the retracted position by detaching the base from the surface of the needle penetrating site. The needle can be biased toward the retracted position.

The method can further comprise locking the needle in the retracted position by providing a needle holder or actuator with a pin and engaging the pin into a horizontally oriented slot formed in the housing, and can further comprise automatically rotating the needled holder or actuator so that the pin engages the slot.

In another aspect, a method of retracting a needle of a needle device can comprise: positioning the housing base to the surface site; providing a needle mounted for a movement between a retracted position in the housing and an extended position, where a portion of the needle extends through the opening in the base; and automatically covering the opening after the needle is moved from the extended position to the retracted position. The needle can be also biased toward the retracted position.

In another aspect, a method of retracting a needle of a needle device can comprise: positioning the housing base to the surface site; providing a needle mounted for a movement between a retracted position in the housing and an extended position, where a portion of the needle extends through the opening formed in the base; and bending the needle to misalign the needle from the needle opening formed in the base when the needle is moved to the extended position after the needle is moved from the extended position back to the retracted position. The needle can be also biased toward the retracted position.

In another aspect, a method of rendering a needle device inoperative can comprise: positioning the housing base to surface site; providing a needle mounted for a movement between a retracted position in the housing and an extended position, where a portion of the needle extends through the opening formed in the housing base; providing an actuator movably mounted to the housing for moving the needle to the extended position; providing a needle shield movable between a retracted position and an extended position; and moving the needle shield to the extended position upon removing the base from the site surface. The needle can be also biased toward the extended position.

The method can further comprise biasing the needle shield toward the extended position so that the needle shield is moved to the extended position upon the base being released from the site surface, after moving the needle to the extended position.

Alternatively, the method can further comprise: adhering the base and a lower end of the needle shield to the site surface; enabling the needle shield to move freely toward the extended position when the needle is moved to the extended position; and maintaining the lower portion of the needle shield adhered to the surface site while removing the base from the surface site to pull out the needle shield and cover the needle. The method can further include propelling the needle to the extended position using a spring.

BRIEF DESCRIPTION OF THE DRAWINGS

These and other features, aspects, and advantages of the present invention will become more apparent from the following description, appended claims, and accompanying exemplary embodiments shown in the drawings, which are briefly described below.

FIG. 21 schematically illustrates a cross-sectional view of yet another embodiment of the needle retraction device according to yet another aspect of the present invention, where the needle is in a stowed, ready to use position.

FIG. 22 schematically illustrates a cross-sectional view of the needle retraction device of FIG. 21, but with the needle in the actuated position, where the needle can penetrate through the skin of a patient's body.

FIG. 23 schematically illustrates a cross-sectional view of the needle retraction device of FIG. 21, but with the needle automatically moved to the retracted position.

FIG. 32 schematically illustrates a cross-sectional view of the needle-enveloping device taken along line 32-32 of FIG. 31, where the needle is in a stowed, ready-to-use position.

FIG. 33 is a view similar to FIG. 32, but illustrates a different cross-sectional view taken along line 33-33 of FIG. 31.

FIG. 34 schematically illustrates a cross-sectional view of the needle enveloping device taken along line 33-33 of FIG. 31, but with the needle in the actuated position, penetrating through the skin of a patient's body.

FIG. 35 schematically illustrates a cross-sectional view of the needle enveloping taken along line 33-33 of FIG. 31, but with its needle shield automatically extended outwardly to shroud the needle.

DETAILED DESCRIPTION

Figure 1:
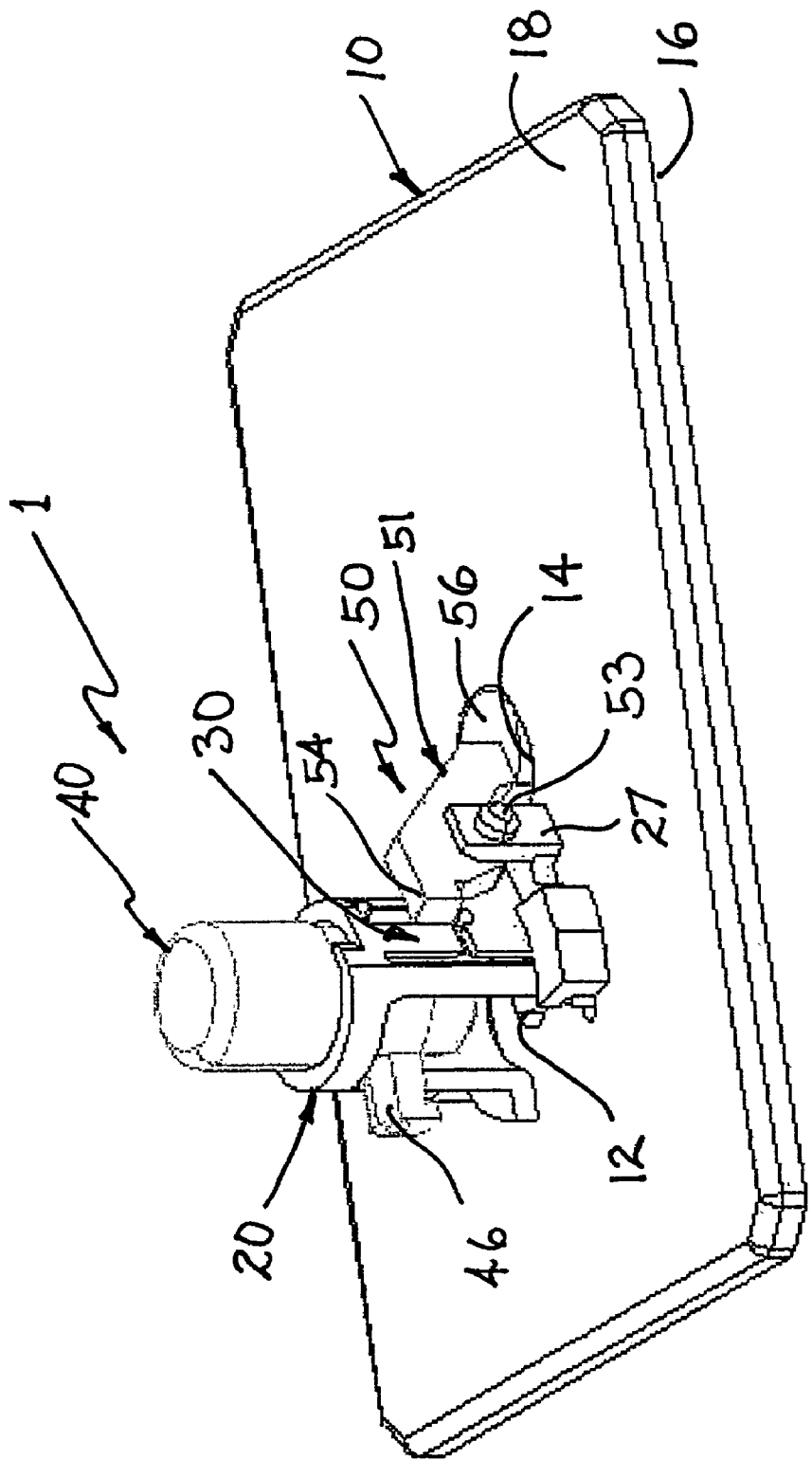
FIG. 1 illustrates a perspective view of a first embodiment of a needle retraction device according to the present invention.
Figure 2:
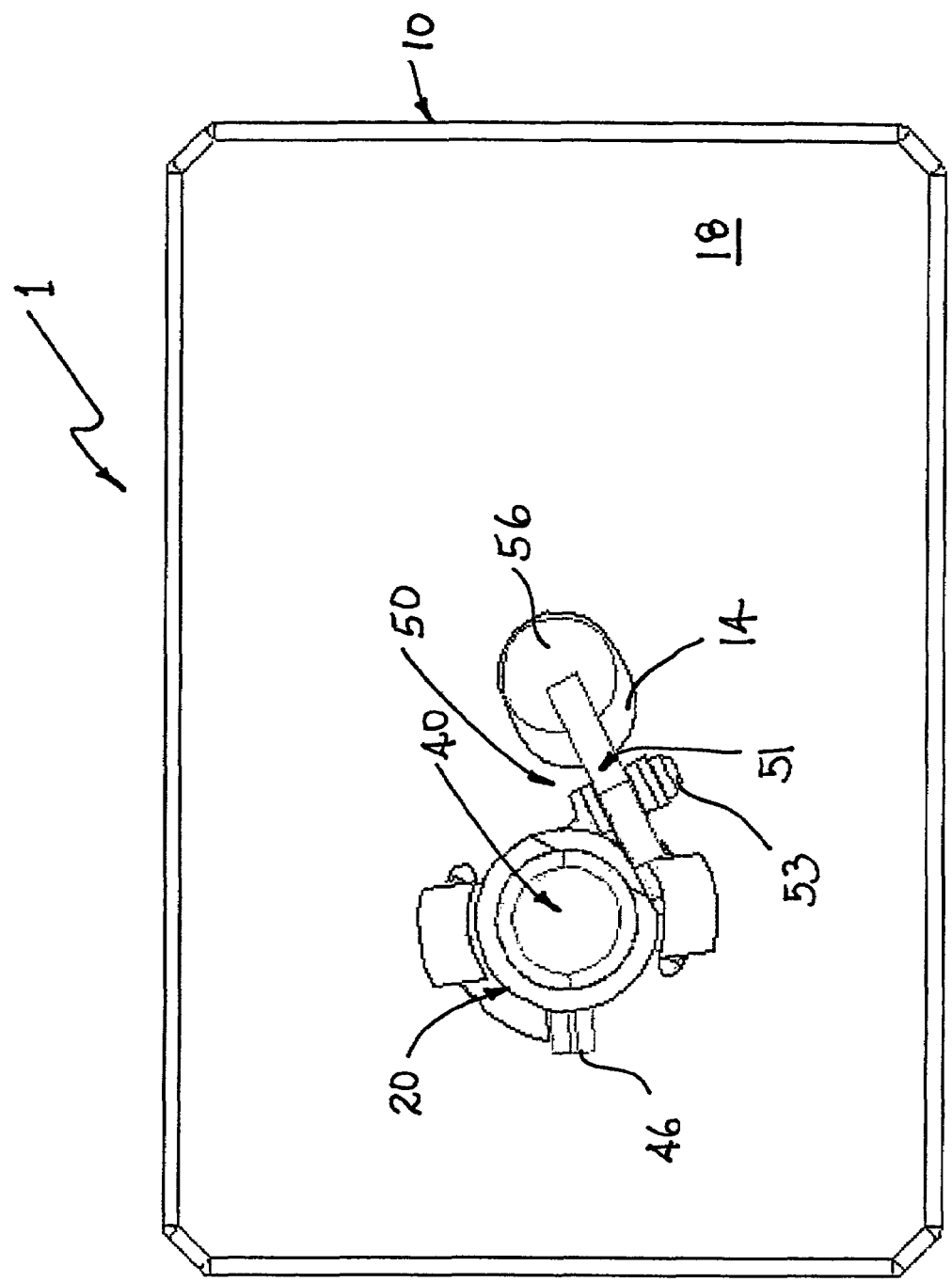
FIG. 2 illustrates a top view of the needle retraction device of FIG. 1.
Figure 3:
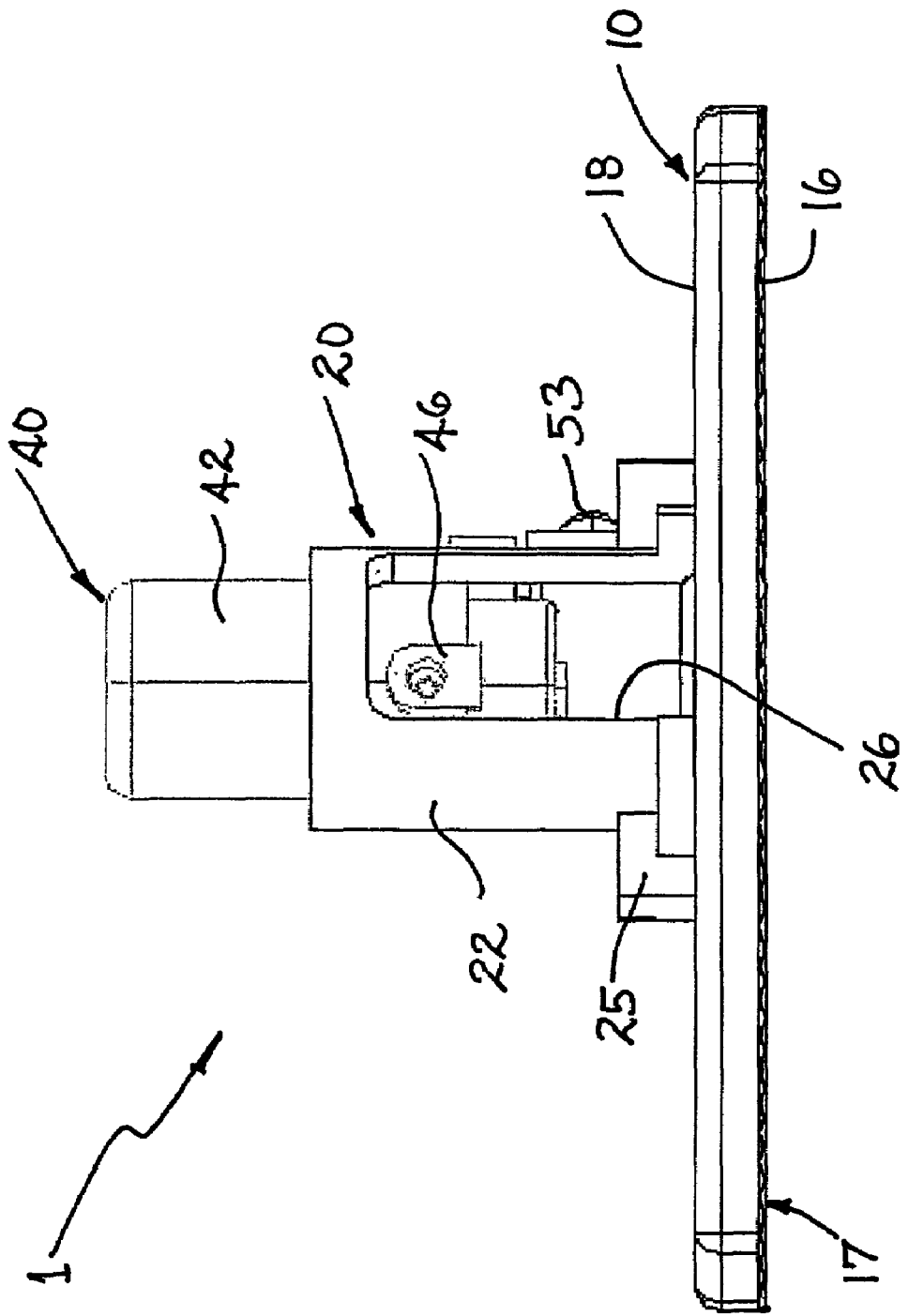
FIG. 3 illustrates a side view of the needle retraction device of FIG. 1.
Figure 4:
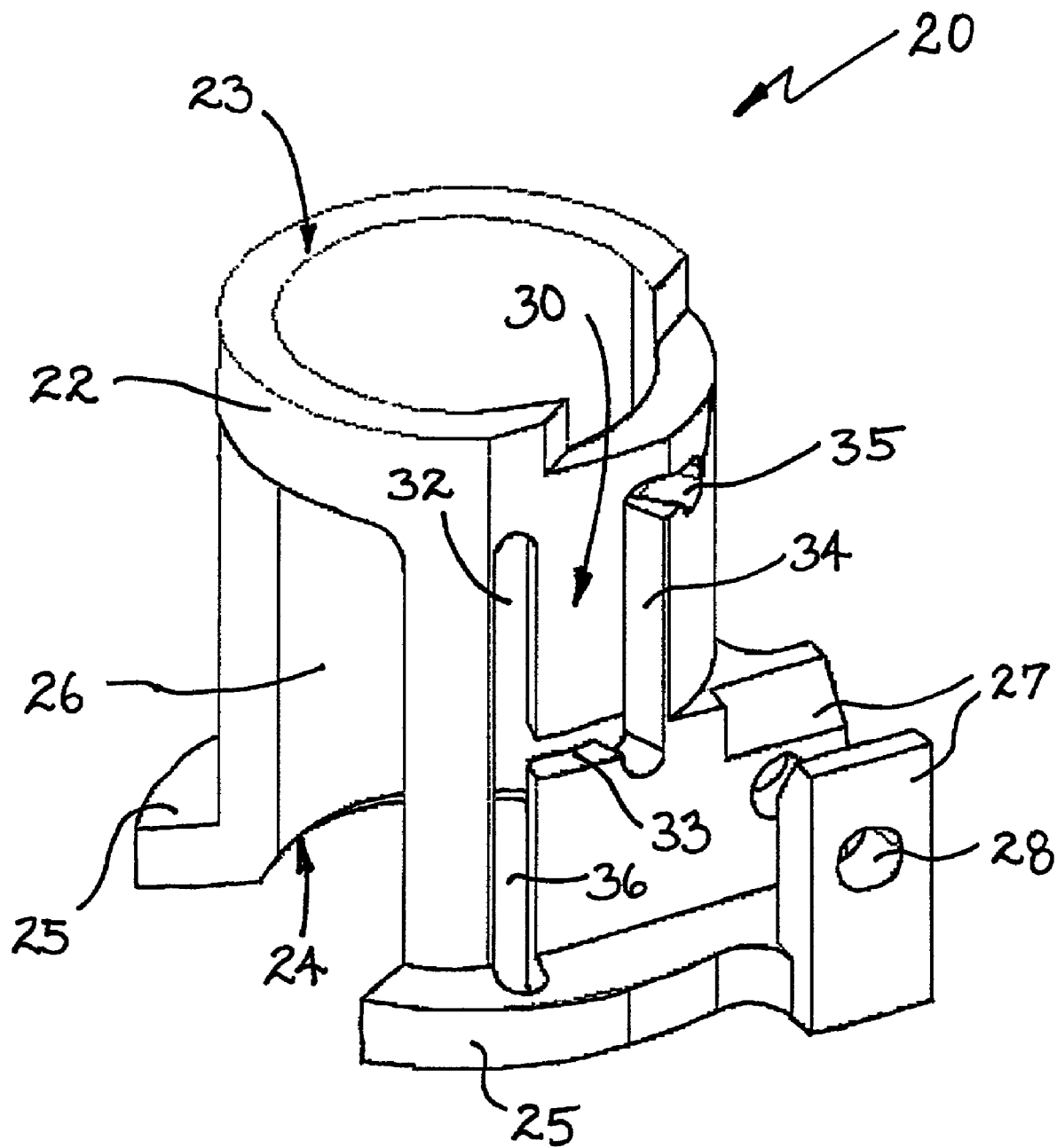
FIG. 4 illustrates a housing component of the needle retraction device of FIG. 1.

Eight exemplary embodiments, as shown in FIGS. 1-36, illustrate preferred embodiments of the needle device 1-8 according to the present invention. Reference numerals 1-8 are also used to designate the respective embodiments. The needle devices 1-8 disclosed herein can be adapted for delivering medication (drug) or fluids to a human patient, or for other uses, such as delivering drug or fluid to other mammals. The needle device 1-8 can be used with a needle N or alternative penetrating member to penetrate through the skin and deliver drug or medication to a patient.

The drug or medication mentioned herein can include any therapeutic agent, which can be a pharmaceutical agent, including biologics such as proteins, peptides, and nucleotides, or a diagnostic agent, such as a contrast agent, including x-ray contrast agents. The drug can be selected from a variety of known classes of drugs, including, for example, proteins, peptides, nucleotides, anti-obesity drugs, nutriceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio- pharmaceuticals, sex hormones (including steroids), anti-allergic agents, stimulants and anoretics, sympathomimetics, thyroid agents, vasodilators and xanthines.

A description of these classes of drugs and a listing of species within each class can be found in Martindale, The Extra Pharmacopoeia, Twenty-ninth Edition (The Pharmaceutical Press, London, 1989), specifically incorporated by reference. The drugs are commercially available and/or can be prepared by techniques known in the art.

Same or corresponding elements or components are labeled with the same reference designation. Further, although references are made below to directions in describing the structure, they are made relative to the drawings (as normally viewed) for convenience. The directions, such as left, right, upper, lower, clockwise, counterclockwise, etc., are not intended to be taken literally or limit the present invention in that fashion.

FIGS. 1-16 and 21-30 illustrate various embodiments 1, 2, 3, 5, 6, and 7 of a needle retraction device, where the needle N automatically retracts, safely away into its housing 20, 120, 330, 430, 530 immediately upon disassociating the surface of the retraction device from a surface of the body B. That is, detaching the retraction device from the penetration site automatically withdraws the needle N. This way, there is no need for the user to discern about manually having to retract, cover or remove the needle N, thereby preventing any injury or health risk to the user or caregiver.

FIGS. 17-20C and 31-36 illustrate various embodiments 5 and 8 of a needle enveloping device, where its needle shield automatically envelops or shrouds the needle N upon disassociating the surface of the retraction device from a surface of the body B.

First Embodiment

Referring to FIGS. 1-9, the first embodiment of the automatic needle retraction device 1 comprises a base 10, a housing 20 attached to the base 10, an actuator 40 mechanically associated with a needle N for moving the needle N, and a retraction mechanism 50 for automatically withdrawing the needle N.

The base 10 can be substantially flat and flexible to enable the same to adhere to and follow the contour of the patient's body part. The illustrated base 10 is substantially rectangular, but can have any desired form suitable for its intended application. Referring to FIGS. 1 and 7-9, the base 10 has a first through hole 12 aligned with the needle N and a second through hole 14 aligned with a component of the retraction mechanism 50. The base 10 can have an attaching device that secures the retraction device 1 to the surface of the patient's skin for a prolonged period. The attaching device, for instance, can be an adhesive layer 17 (see FIG. 3) provided on an outer or lower surface 16 of the base 10. The first and second through holes 12, 14 also extend through the adhesive layer 17. The adhesive layer 17 can be covered with a protective layer (not shown), which also covers the first and second through holes 12, 14. Alternatively, the attaching device can be a strap, tape, band, or the like (not shown), which allows the patient to secure the device 1 to the surface of a desired body site.

Although not shown, the needle can also be provided with a removable protective sheath, which is removed before use. The protective sheath can protrude beyond the base lower surface 16 or the protective layer for ease of its removal. Alternatively, the protective layer can be attached to the protective sheath so that removing the protective layer automatically detaches the protective sheath from the needle N.

The housing 20, which is secured to the base 10 or integrally formed with the base 10, guides the actuator 40. The housing 20 comprises, as better illustrated in FIG. 4, a substantially hollow cylindrical or tubular housing body 22 having an upper open end 23 and a lower open end 24. The lower end 24 can have a flange 25 or the like extending radially outwardly to more stably support the housing 20 to an upper surface 18 of the base 10. The housing body 22 also has a slot 26 extending from near its upper end 23 to its lower 24, and an actuator guide 30 comprising a continuous slot formed through the housing body 22 for guiding the actuator 40 to take a particular path of movement. That is, the actuator guide 30 is configured to guide the actuator 40 along a path that can maintain the needle N at its injection position, without having to manually hold the needle down, and permanently lock the actuator 40 and the needle to its retracted position automatically after use or after it is actuated. See FIG. 9.

Referring to FIGS. 4 and 7-9, the actuator guide 30 comprises a substantially U-shaped slot or channel (32, 33, 34). The actuator guide 30 comprises a first vertical portion 32 extending vertically between the first and second ends 23, 24 of the tubular body 22, a second vertical portion 34 extending substantially parallel with the first vertical portion 32, and a first horizontal portion 33 connecting about the lower end of the first vertical portion 32 and the lower end of the second vertical portion 34. The first vertical portion 32 can have a lower extension 36 extending continuously therefrom, below the first horizontal portion 33, to the flange 25. The lower vertical extension 36 can allow easier assembly of the actuator 40 into the housing 20 through its lower end 24. That is, the lower extension 36 can accommodate a pin 44 extending radially outwardly from the actuator 40. See FIG. 5. The second vertical portion 34 has a locking portion 35 extending laterally or horizontally from its upper end, away from the first vertical portion 32. The actuator guide 30 controls the motion of the actuator 40 as the actuator 40 is pushed down and automatically retracted up.

Figure 5:
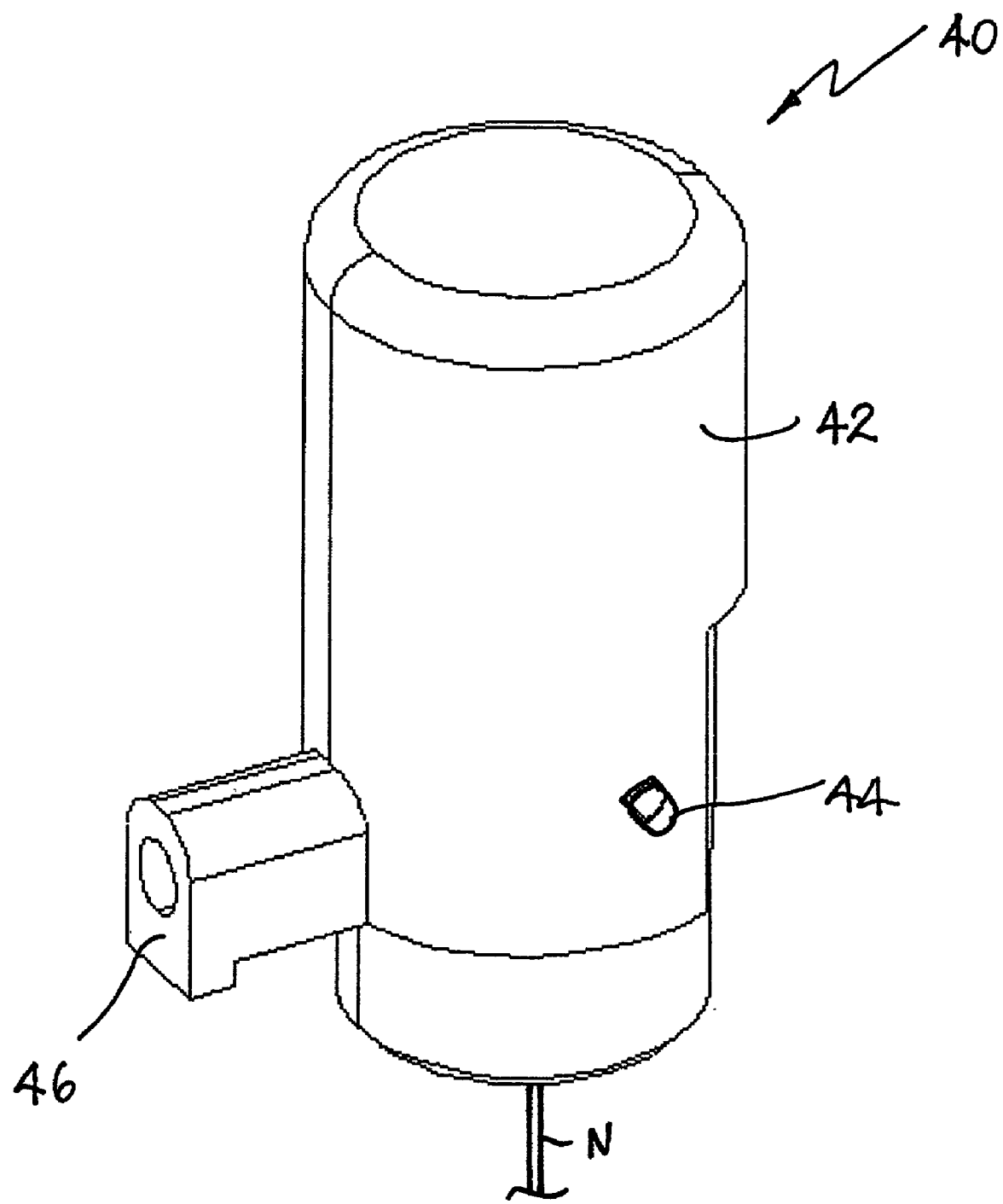
FIG. 5 illustrates an actuator component of the needle retraction device of FIG. 1.
Figure 7:
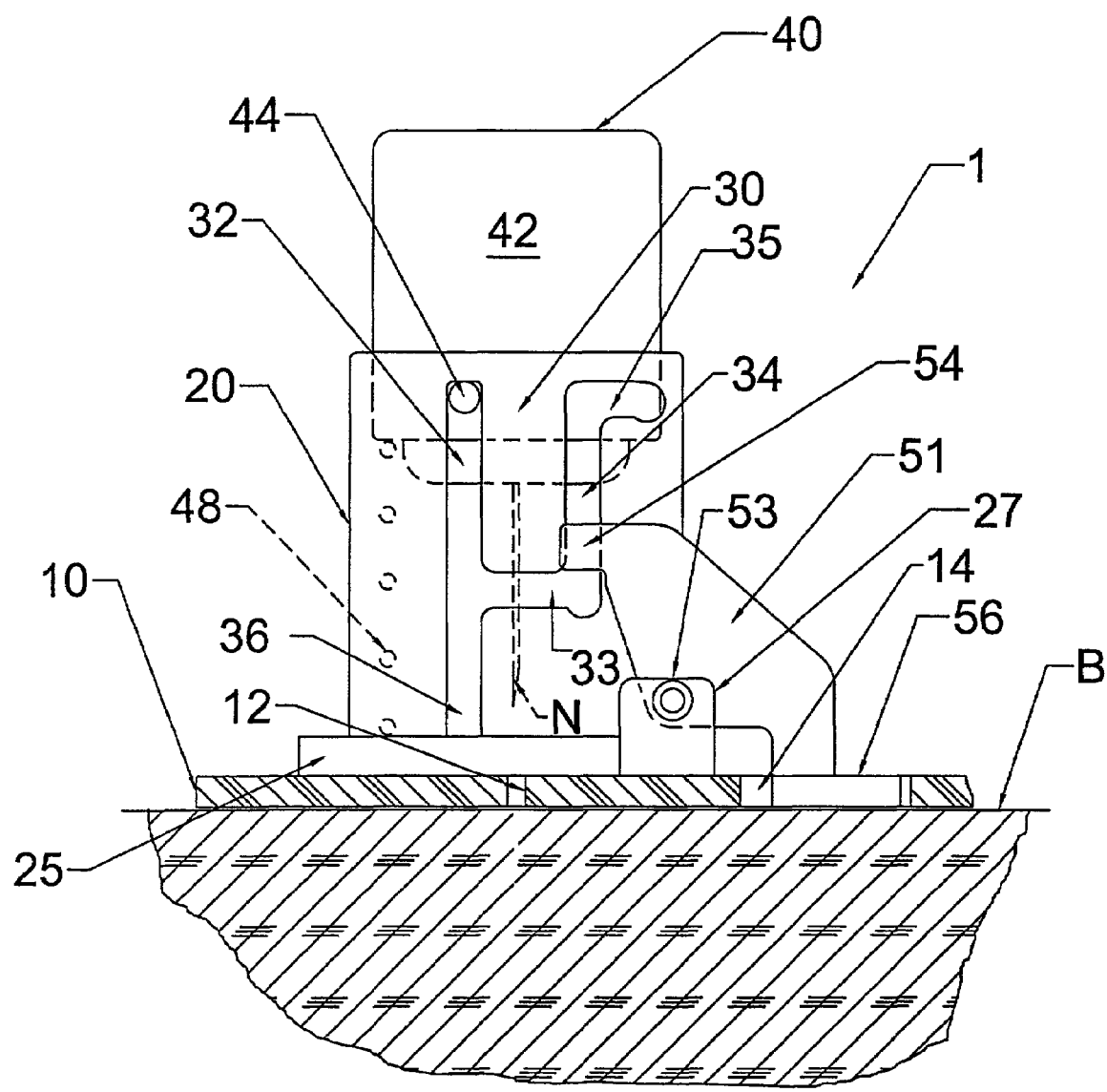
FIG. 7 schematically illustrates the needle retraction device of FIG. 1, where the needle is in a stowed, ready-to-use position.
Figure 8:
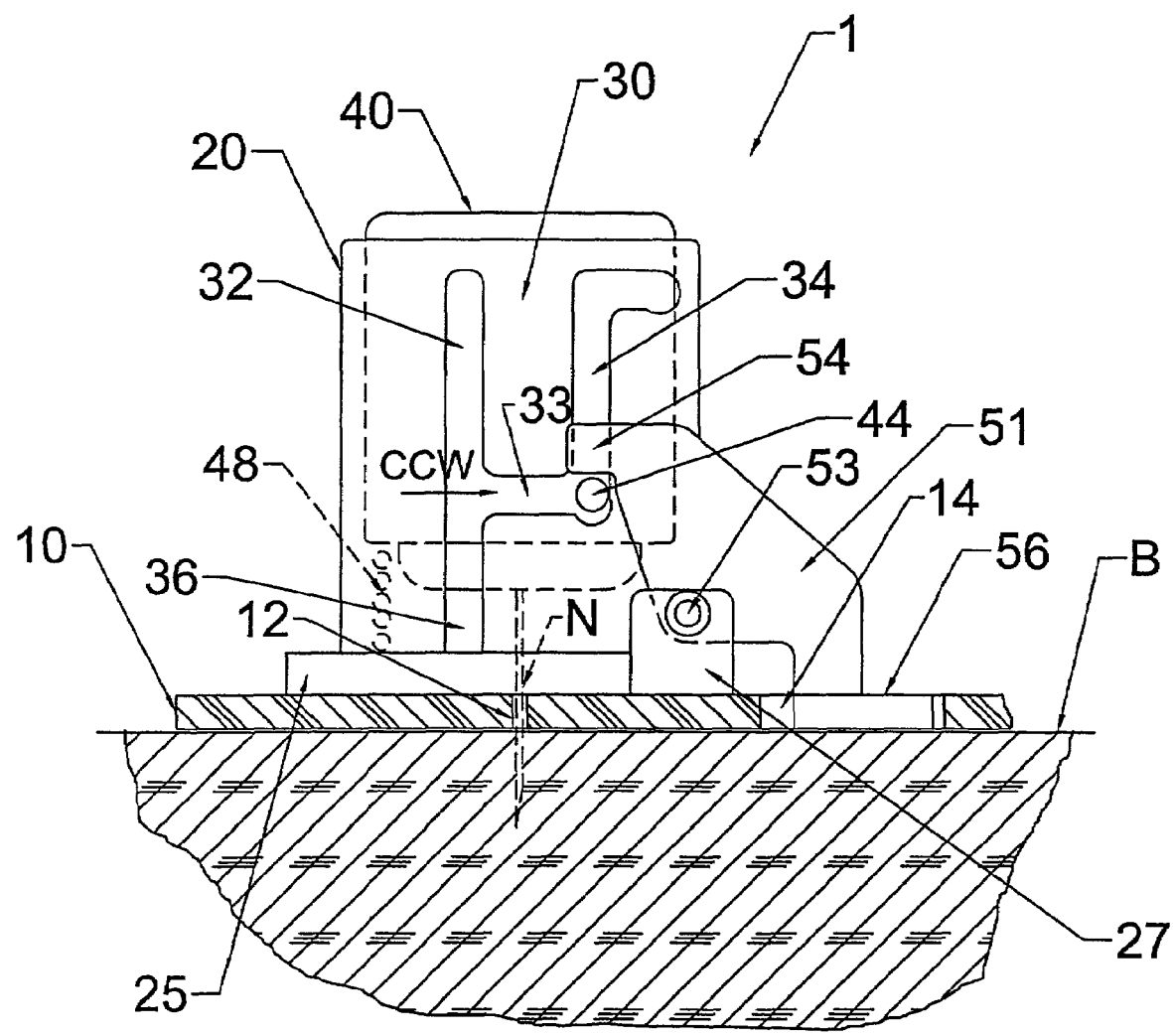
FIG. 8 schematically illustrates the needle retraction device of FIG. 1, but with the needle in the actuated position, penetrating through the skin of a patient's body.
Figure 9:
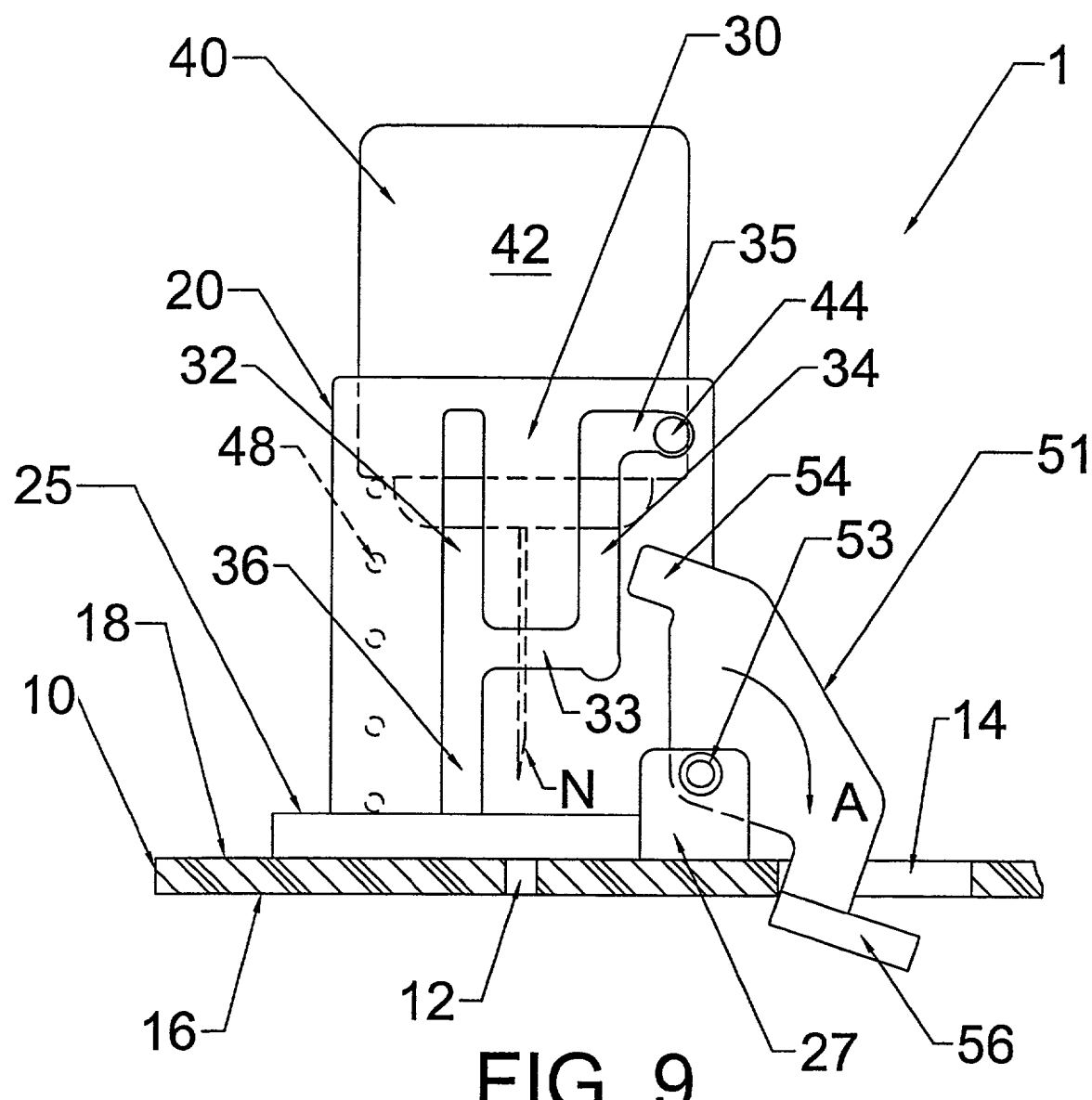
FIG. 9 schematically illustrates the needle retraction device of FIG. 1, but with the needle automatically moved to the retracted position.
Figure 10:
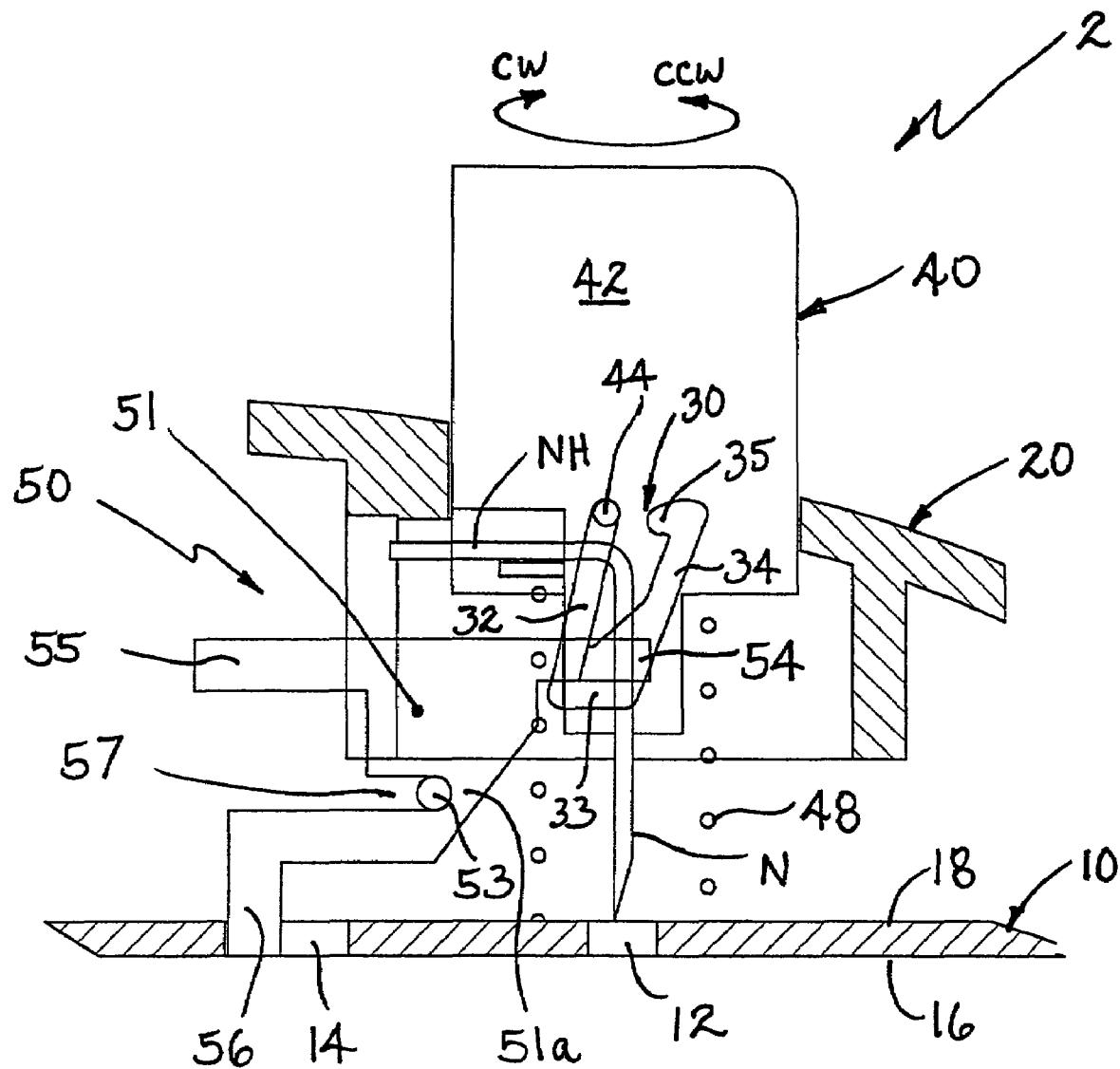
FIG. 10 schematically illustrates a cross-sectional view, illustrating a second embodiment of the needle retraction device according to the present invention, where the needle is in a stowed, ready-to-use position.

Referring to FIG. 5, the actuator 40 comprises an actuator body 42 connected to the needle N and movably mounted to the housing 20 between an actuated or pushed position where the needle N is in the extended position as shown in FIG. 8 and unactuated or out position where the needle N is in the retracted position as shown in FIG. 7. A guide pin 44 is dimensioned to extend radially outwardly from the actuator body 42 and extend through the actuator guide 30. The pin 44 can be rigidly attached to the actuator body 42 or spring loaded so that it can retract into the actuator body 42 to assist engagement of the pin 44 with a component of the retraction mechanism 50. The actuator body 42 is inserted into the housing body 22 through its lower end 24, with the pin 44 inserted into the actuator guide 30 to enable the actuator body 42 to follow the path of the actuator guide 30 as the actuator body 42 is depressed and released, e.g., vertically moved, as shown in FIGS. 7-9. The lower vertical extension 36 extending below the first horizontal guide portion 33 allows the pin 44 to be guided up into the substantially U-shaped actuator guide 30 when the actuator 40 is inserted into the housing 20 during assembly. If the pin 44 is retractable, the lower vertical extension 36 can be eliminated since the pin 44 can be retracted into the actuator body 42 to allow the same to slide inside the housing body 22. That is, the inside surface of the housing 20 can abut against the pin 44 and slide therealong until the pin 44 reaches the first vertical portion 32.

Referring to FIGS. 1, 3, 4, and 5, the actuator body 42 has a medication port 46. The medication port 46 extends radially outwardly therefrom and cooperates with the housing slot 26, which is dimensioned to provide clearance for the port 46 to vertically move and rotate with the actuator 40 within the confines of the slot 26. The medication port 46 can be connected to fluidly communicate with a drug reservoir (not shown) containing liquid drug under pressure. The medication port 46 is in liquid communication with the needle N.

The needle N is fixedly attached to the actuator body 42. The port 46 is in communication with the needle N by means of a channel, or the needle may be directly fixed to the port. In the first embodiment, the needle N is straight and is fixed at one end to the actuator body 42 and the needle is in liquid communication with the port 46. However, in the second embodiment described below, the needle N is angled, substantially L-shaped, as shown in FIGS. 10-13. As shown in FIGS. 10-13, a horizontal leg portion NH of the needle can be fixedly mounted or embedded into the medication port 46.

Returning to the first embodiment (FIGS. 7-9), a spring 48, which is preloaded torsionally and axially, is positioned between the actuator body 42 and the base upper surface 18, and confined within the housing 20. The spring 48 can be a conventional compression spring that can apply a torsional force by twisting the spring 48. The spring 48, which is located parallel to the longitudinal axis of the needle N, biases the actuator 40 upwardly or away from the base 10 to thereby maintain the attached needle N away from the patient, in the withdrawn or stowed position, safely retracted within the housing 20 as shown in FIG. 7. The lower end of the spring 48 is preferably attached to the base 10 and the upper end of the spring 48 is preferably attached to the actuator body 42. This way, rotating the actuator body 42 relative to the base 10 creates a torsional load. A torsional preload can be applied by rotating the actuator body 42 by a desired degree, such as a quarter, third, half, etc., of a turn, and positioning the pin 44 in the first vertical portion 32 while the spring 48 is in the torsionally preloaded (rotated) state.

Referring to FIGS. 1, 6, and 7-9, the retraction mechanism 50 includes a trigger member 51 engageable with the pin 44 to maintain the actuator 40 in the injection position, without having to manually hold down the actuator 40. The trigger member 51 is releasable from the pin 44 to allow the actuator 40 to retract upwardly. The trigger member 51 is movably mounted relative to the housing 20 or the base 10. In this respect, either the base 10 or the housing 20 can include a pair of upright members or ears 27 or the like (see FIG. 4), with through holes 28 for pivotally mounting the trigger member 51. The trigger member 51 (shown in detail in FIG. 6) has a through hole 52 alignable with the ear through holes 28 (see FIG. 4) for receiving a pivot pin 53.

Figure 6:
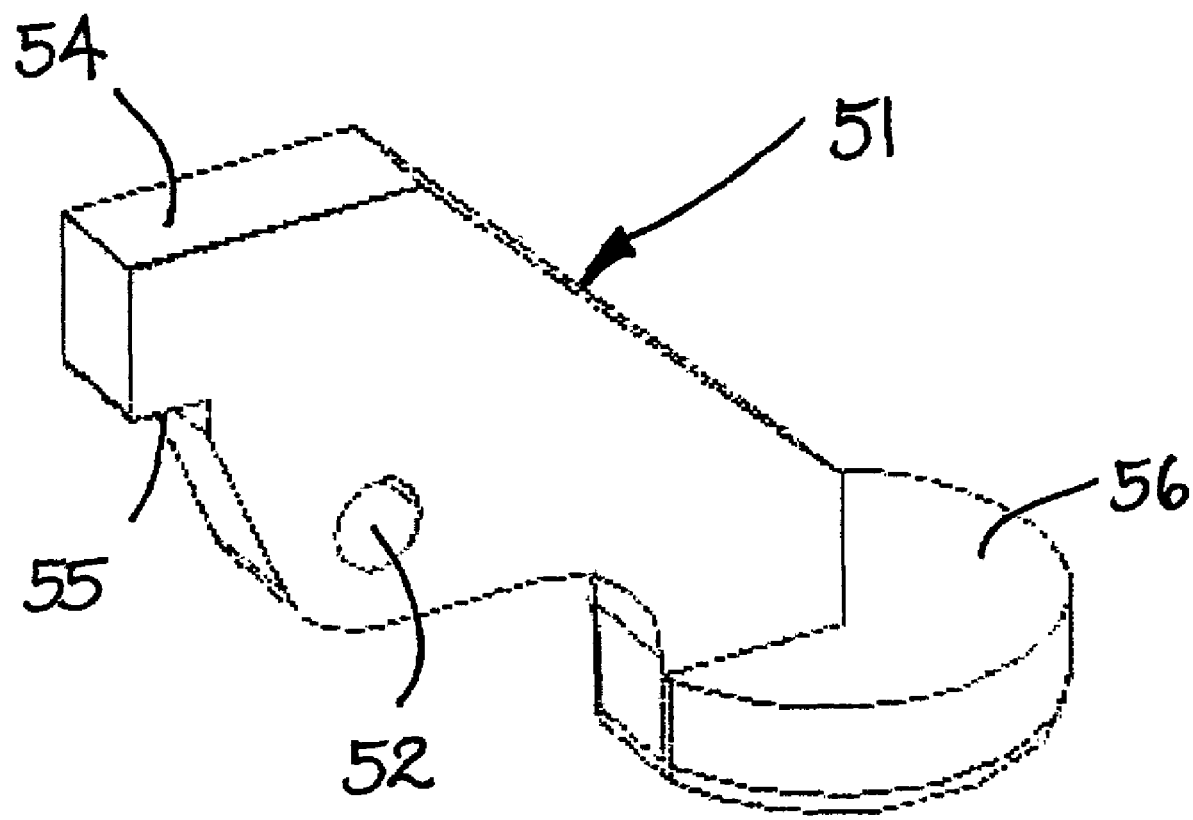
FIG. 6 illustrates a trigger member component of the needle retraction device of FIG. 1.

Referring FIG. 6, the trigger member 51 has a first portion 54 and a second portion or foot 56. The foot 56 is adapted to contact the surface of the body B. The first portion 54 is adapted to hold down the actuator 40 by holding down the pin 44, when the actuator 40 is pushed fully down to the actuated position (the needle N in the extended position), as shown in FIG. 8. This prevents the actuator 40 from moving up to the out position (the needle in the retracted position), as shown in FIG. 9, while the foot 56 engages the surface of the body B (when the base 20 is attached to the surface of the body B). The first portion 54 has a pin engaging surface 55 that receives the pin 44 thereon. The foot 56 extends through the second through hole 14 formed in the base 10 to contact the surface of the body B and prevents the trigger member 51 from rotating clockwise (see arrow A in FIG. 9). If the base 20 is moved away from the patient before completing delivery of the drug to the patient, such as when pulling off the device 1 from the patient, since the body B no longer blocks the foot 56, the spring 48, which upwardly urges the actuator 40, forces the trigger member 51 to rotate clockwise (referring to FIG. 9) to automatically retract the actuator 40, and the needle N into the housing 20.

The operation of the first embodiment will be referred to FIGS. 7-9. The needle retraction device 1 is positioned to a patient's injection site, as shown in FIG. 7 by exposing the adhesive layer 17 (FIG. 3) to the skin surface of the body B, as shown in FIG. 7. In the ready-to-use state, the actuator 40 is fully extended upwardly and the needle N is in its stowed position, safely within housing 20. Once the device 1 is secured to the skin surface of the body B, the user depresses the actuator 40 along the top surface thereof, against the force of the spring 48, compressing the spring 48, as shown in FIG. 8. Depressing the actuator 40 also moves the needle N downwardly through the first aperture 12 and penetrates into the body B.

As the actuator 40 is being depressed, the pin 44 is guided in the first vertical guide portion 32 of the actuator guide 30. The spring 48 is both torsionally (in the clockwise direction L referring to FIGS. 7 and 8) and axially preloaded. As the actuator 40 moves down along the first vertical guide portion 32 and when the pin 44 reaches the horizontal guide portion 33 of the actuator guide 30, the torsional force of the spring 48 rotates the actuator 40 opposite to the torsional energization direction (counterclockwise CCW—see FIG. 8). By fixing the upper end of the spring 48 to the actuator body 42 and fixing the lower end of the spring 48 to the base 10, the torsional force of the spring 48 created by the rotated actuator 40 enables the actuator 40 to rotate in the opposite direction.

The spring torsional and the axial forces allow the pin 44 to follow the guide slot configuration, e.g., U-shape, of the actuator guide 30. Once the pin 44 moves down to the horizontal guide portion 33, the spring 48 moves the pin 44 to the position where it can be guided in the second vertical guide portion 34. Because the foot 56 of the trigger member 51 engages the skin surface of the body B through the second through hole 14 formed in the base 10, the trigger member 51 cannot rotate clockwise (FIG. 8). When the pin 44 reaches or is near the second vertical portion 34, the first trigger member portion 54 lies above the pin 44 (FIG. 8), blocking the pin's pathway in the second vertical guide portion 34 and preventing the pin 44 from moving up along the second vertical guide portion 34. Thus, the trigger member 51 maintains the actuator 40 and the needle N in the injection position, as shown in FIG. 8. In the injection position shown in FIG. 8, the needle N can deliver drug to the user through the port 46. This position is held throughout delivery mode without having to manually hold down the actuator 40.

Referring to FIG. 9, upon removing the device 1, whether accidentally or deliberately, away from the skin surface of the body B, the needle N will automatically retract into the housing 20. When the base 10 is removed away from the body B, the foot 56 has no support to abut itself against. Without this support, the trigger member 51 becomes free to rotate clockwise A about the pivot pin 53 (FIG. 8). Rotating the trigger member 51 in the clockwise direction A releases the pin 44. With the pin 44 free from the first portion 54, the actuator 40 moves up, withdrawing the needle N from body B and retracting the needle N into the housing 20. More specifically, the trigger member 51 will be permitted to rotate through the second through hole 14 as the spring 48 moves the actuator 40 up and moves the pin 44 up along the second vertical guide portion 34.

Once the pin 44 reaches the top of the second vertical portion 34, the remaining torsional force of the spring 48 forces the actuator 40 to further rotate counterclockwise CCW and move the pin 44 into the lateral locking portion 35. When the pin is in the locking portion 35, the torsional force of the spring 48 immobilizes the pin 44 in the locking portion 35, thereby preventing the actuator 40 to moving vertically and rendering the needle retraction device 1 unusable.

This locking feature enables the delivery of drug to occur once and prevents tampering with the device once delivery is complete. If the system is accidentally removed, it cannot be reused as such reuse could introduce harmful bacteria and pathogens into the user's system.

Second Embodiment

FIGS. 10-13 schematically illustrates the second embodiment of the needle retraction device 2 according to the present invention. The base 10 and the housing 20 of the second embodiment are substantially similar to that of the first embodiment 1. The housing 20, like that of the first embodiment 1, has an actuator guide 30 designed to guide the actuator 40 vertically and rotationally. The primary differences between the first embodiment 1 and second embodiment 2 lies in the actuator guide configuration and the trigger member 51, while maintaining substantially the same operation principle. In the second embodiment 2, the first and second vertical guide portions 32, 34 are angled or slanted, and the trigger member 51 further includes means for manually retracting the needle while the device 2 remains attached to the patient.

The actuator 40 of the second embodiment also comprises an actuator body 42 connected to the needle N, as previously described in the first embodiment 1. This actuator 40 is vertically movably guided in the housing 20. A guide pin 44 extends radially outwardly from the actuator body 42, similar to the actuator body 42 of the first embodiment 1. Again, the pin 44 can be rigidly attached to the body 42 or spring loaded so that it can retract into the actuator body 42 to assist engagement of the pin 44 with its trigger member 51. The actuator body 42 is inserted into the housing 20 so that the pin 44 is inserted into the first vertical portion 32 of the actuator guide 30 to enable the actuator body 42 to follow the path of the actuator guide 30 as the actuator body 42 is depressed and released, e.g., vertically moved, as shown in FIGS. 10-13.

The actuator body 42 also has a medication port (not shown) substantially similar to the one shown in FIG. 5. The housing 20 has a slot or opening (not shown), dimensioned to provide clearance for the port to vertically move and rotate along with the actuator 40. The needle N is fixedly attached to the actuator body 42, with one end thereof communicating with the port and the other end adapted to penetrate into the patient, through the first through hole 12, as substantially illustrated in FIGS. 10-13. Here, the needle N is angled, substantially L-shaped. The horizontal leg portion NH of the needle N is fixedly mounted or embedded into the medication port.

The actuator guide 30 comprises a substantially U-shaped slot or channel (32, 33, 34) formed in the housing 20. The actuator guide 30 comprises a first slanted vertical guide portion 32 extending within the housing 20, a second slanted vertical guide portion 34 extending substantially parallel with the first slanted vertical guide portion 32, and a first horizontal guide portion 33 connecting about the lower ends of the first and second slanted vertical guide portions. The second vertical guide portion 34 has a locking portion 35 extending laterally or horizontally from its upper end, toward the first vertical guide portion 32. The actuator guide 30 controls the motion of the actuator 40 as the actuator is pushed down and retracted up, as in the first embodiment 1.

The retraction mechanism 50 includes a trigger member 51 engageable with the pin 44 to maintain the actuator 40 in the injection position, without having to manually hold down the actuator 40, as in the first embodiment 1. The trigger member 51 is releasable from the pin 44 to allow the actuator 40 to retract upwardly. The trigger member 51 is movably mounted relative to the base 10 or the housing 20, similar to the first embodiment 1.

The trigger member 51 of the second embodiment 2 is substantially similar to that of the first embodiment 1, including the first portion 54 and the second portion or foot 56, as described previously. In the second embodiment, the foot 56 extends through the second through hole 14 formed in the base 10 to contact the surface of the body B and prevent the trigger member 51 from rotating counterclockwise direction about its pivot pin 53 (referring to FIGS. 10-13). As in the first embodiment 1, if the base 20 is moved away from the patient before completing delivery of the drug to the patient, such as when pulling off the device 2 from the patient, since the foot 56 is not blocked, the spring 48, which upwardly urges the actuator 40, forces the trigger member 51 to rotate counterclockwise (referring to FIG. 12) to automatically retract the actuator 40, and the needle N into the housing 20.

Figure 13:
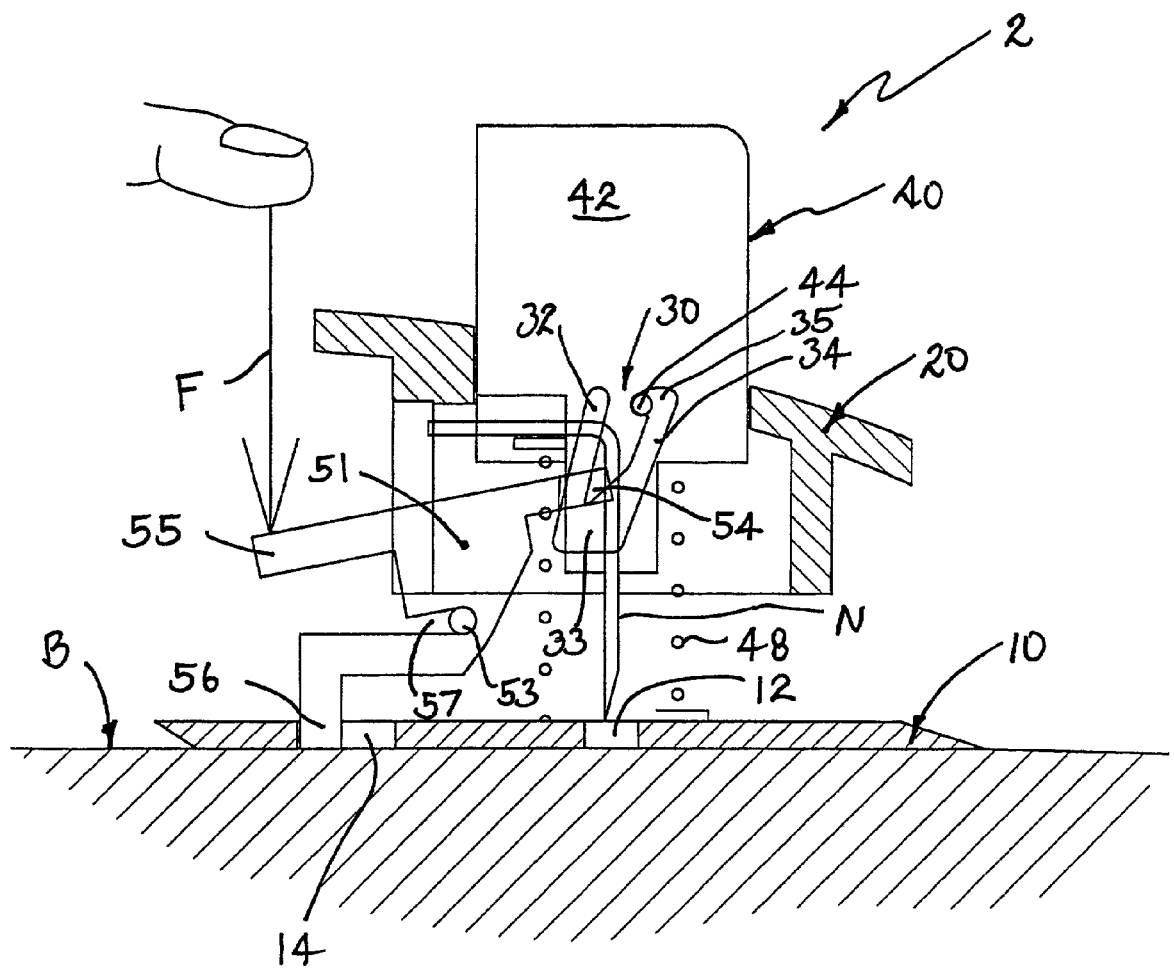
FIG. 13 schematically illustrates a cross-sectional view of the needle retraction device of FIG. 10, where the needle has been manually retracted.

Referring to FIG. 13, in the second embodiment 2, the trigger member 51 further includes a manual actuation lever 55 that can manually withdraw or retract the needle actuator 40 while the device 2 is attached to the patient. In this respect, the trigger member 51 has a provision for allowing the first portion 54 to move independently of the foot 56. This is achieved by providing a slot 57 that receives the pivot pin 53 instead of the through hole 52 (first embodiment). Providing the slot 57, and leaving a relatively thin portion 51*a* adjacent the end of the slot 57 allows the first portion 54 of the trigger member 51 to bend or flex relative to the foot portion 56 about the pivot pin 44. That is, part of the trigger member 51 above the pin 53 flexes about the pin 53 when the lever 55 is depressed (as shown in FIG. 13) with a predetermined downward force F, creating a pivoting movement in the first portion 54 to release the pin 44, while the foot 56 remains engaged to the patient. With the actuator 40 free from the constraint of the first trigger member portion 54, the actuator 40 with the needle N can retract, as previously explained with reference to FIG. 9 (first embodiment). The first embodiment can also include a similar trigger arrangement (i.e., slot 57 and a manual lever 55) for manually retracting the needle.

Figure 11:
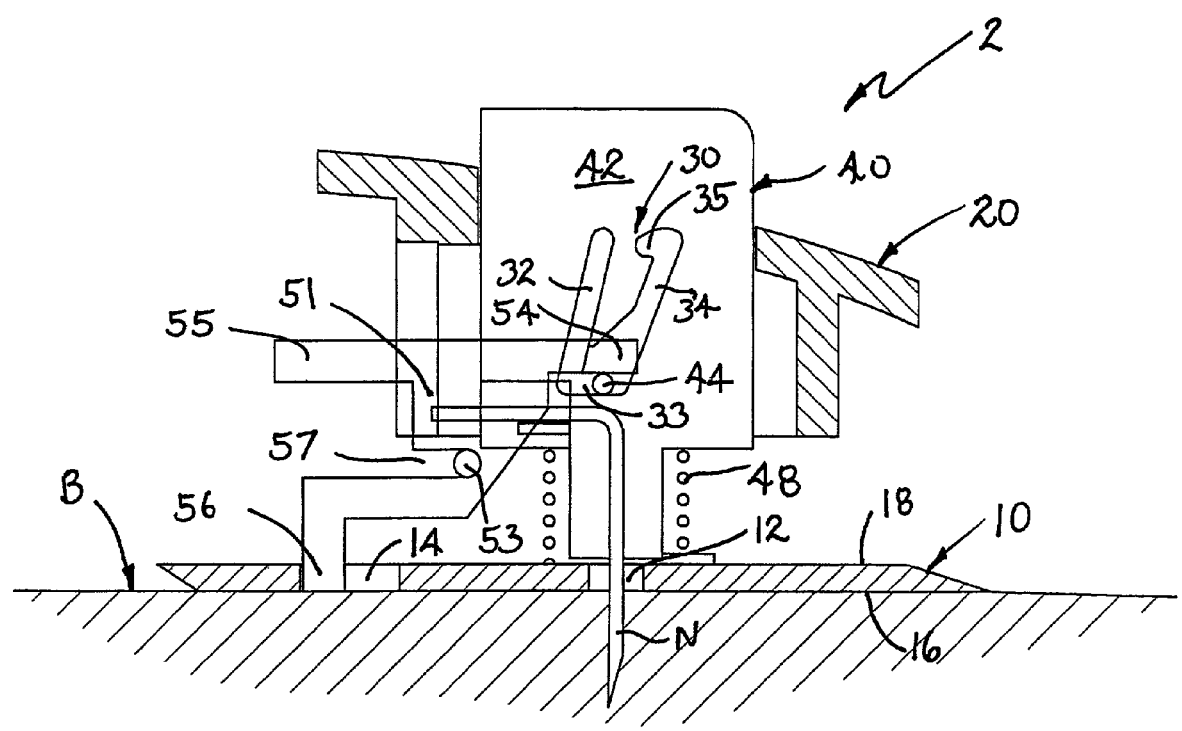
FIG. 11 schematically illustrates a cross-sectional view of the needle retraction device of FIG. 10, but with the needle in the actuated position, penetrating through the skin of a patient's body.

In operation of the second embodiment, referring to FIGS. 10-13, the needle retraction device 2 is positioned to a patient's injection site, as explained in the first embodiment 1. In the ready-to-use state, the actuator 40 is fully extended upwardly and the needle N is in its stowed position, safely within housing 20. Once the device 2 is secured to the skin surface of the body B, the user depresses the actuator 40 along the top surface thereof, against the force of the spring 48, compressing the spring 48, as shown in FIG. 11. Depressing the actuator 40 also moves the needle N downwardly through the first aperture 12 and into the body B.

As the actuator 40 is being depressed, the pin 44 is guided in the first vertical portion 32 of the actuator guide 30. As the first vertical guide portion 32 is angled from the vertical, moving the actuator 40 down while the pin 44 is guided in the first vertical portion 32 forces the actuator 40 to rotate clockwise CW (referring to FIG. 10), and applies a torsional load. By fixing the upper end of the spring 48 to the actuator body 42 and fixing the lower end of the spring 48 to the base 10, the torsional force of the spring 48 created by the rotated actuator 40 enables the actuator 40 to rotate in the opposite direction, similar to the effect of torsionally preloading the spring 48, as disclosed in the first embodiment.

As the pin 44 is guided in the first vertical guide portion 32, the pin 44 moves past the first trigger member portion 54. In this respect, the first trigger member portion 54 can be designed to flex so that the pin can move past it and continue along its travel path within the actuator guide 30. Alternatively, if the pin 36 is spring loaded, it can be retracted into the actuator body 42 as the end of the pin 44 rubs against the inner sidewall of the first portion 54. The inner sidewall also can be ramped or beveled (not shown), if desired, to allow the pin 44 to retract or urge the pin 44 to clear past the first trigger member portion 54, as the pin 44 is moving downwardly.

As the actuator 40 moves down along the first vertical portion 32, the torsional force of the spring 48 rotates the actuator 40 opposite to the torsional energization direction (counterclockwise CCW (FIG. 10)) when the pin 44 clears the first trigger member portion 54 and reaches the horizontal portion 33 of the actuator guide 30. This moves the pin 44 over to the position where it can be guided in the second vertical portion 34 of the guide 30. In this respect, the lower end of the second vertical guide portion 34 can be beveled into the first horizontal portion 33 to assist the upward guiding of the actuator 40. Because the foot 56 of the trigger member 51 engages the skin surface of the body B through the second through hole 14 formed in the base 10, the trigger member 51 cannot rotate counter clockwise about its pivot pin 53. The first trigger member portion 54 lies above the pin 44 (FIG. 11), blocking the pin's pathway in the second vertical guide portion 34 and preventing the pin 44 from moving up along the second vertical guide portion 34. Thus, the trigger member 51 maintains the actuator 40 and the needle N in the injection position, as shown in FIG. 8. In the injection position shown in FIG. 8, the needle N can deliver drug to the user through its port. This position is held throughout delivery mode without having to manually hold down the actuator 40.

Figure 12:
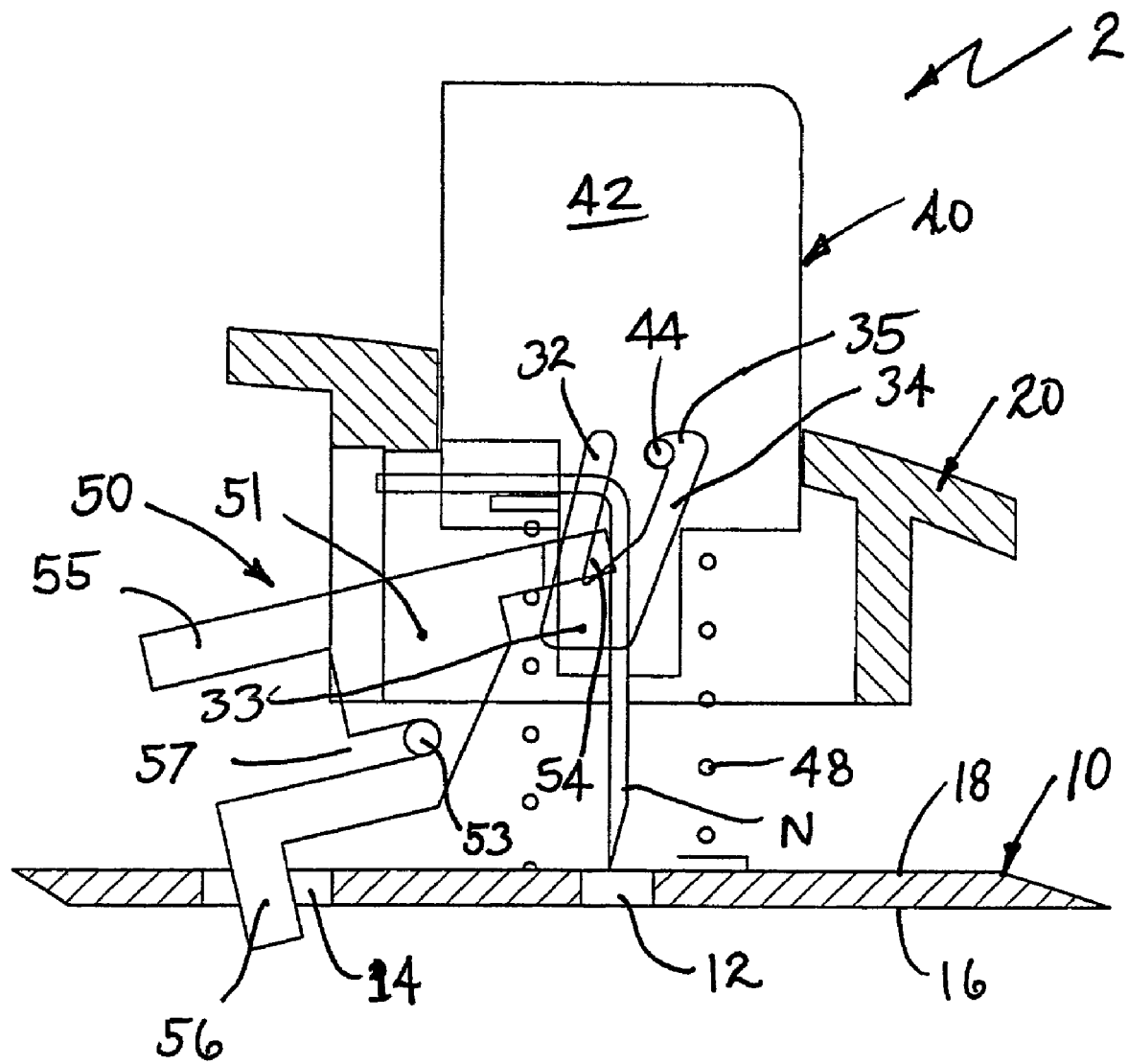
FIG. 12 schematically illustrates a cross-sectional view of the needle retraction device of FIG. 10, but with the needle automatically moved to the retracted position.

Referring to FIG. 12, upon removing the device 2, whether accidentally or deliberately, away from the skin surface of the body B, the needle N will automatically retract into the housing 20. When the base 10 is removed away from the body B, the foot 56 has no support to abut itself against. Without this support, the trigger member 51 becomes free to rotate counterclockwise about the pivot pin 53. Rotating the trigger member 51 in the counterclockwise direction releases the pin 44. With the pin 44 free from the first portion 54, the actuator 40 can move up, withdrawing the needle N from body B and retracting the needle N into the housing 20. More specifically, the trigger member 51 will be permitted to rotate through the second through hole 14 as the spring 48 moves the actuator 40 up, and thus moves its pin 44 up along the second vertical guide portion 34. As the pin 44 is guided up in the second slanted vertical guide portion 34, the actuator 40, with the needle N, is moved up and further rotated counterclockwise CCW, again torsionally loading the spring 48. When the pin 44 reaches the lateral locking portion 35, the torsional load of the spring 48 rotates the actuator 30 clockwise CW and locks the pin 44 in the locking portion 35. In this position, as shown in FIG. 12, the actuator 40 cannot move vertically. This position cannot be altered without destroying the device 2, as is in the first embodiment. Thus, the user will not be able to use the device or even depress the actuator 40.

Referring to FIG. 13, the device 2 can manually retract the needle, while the device 2 is attached to the body B. This can be done by depressing the lever 55 to pivot the first trigger member portion 54 away from the pin 44 while the device 2 is attached to the body B. With the actuator 40 free from the constraint of the first trigger member portion 54, the actuator 40 with the needle N will retract.

As in the first embodiment 1, this locking feature enables the delivery of drug to occur once and prevents tampering with the device once delivery is complete. If the system is accidentally removed, it cannot be reused as such reuse could introduce harmful bacteria and pathogens into the user's system.

Third Embodiment

Figure 14:
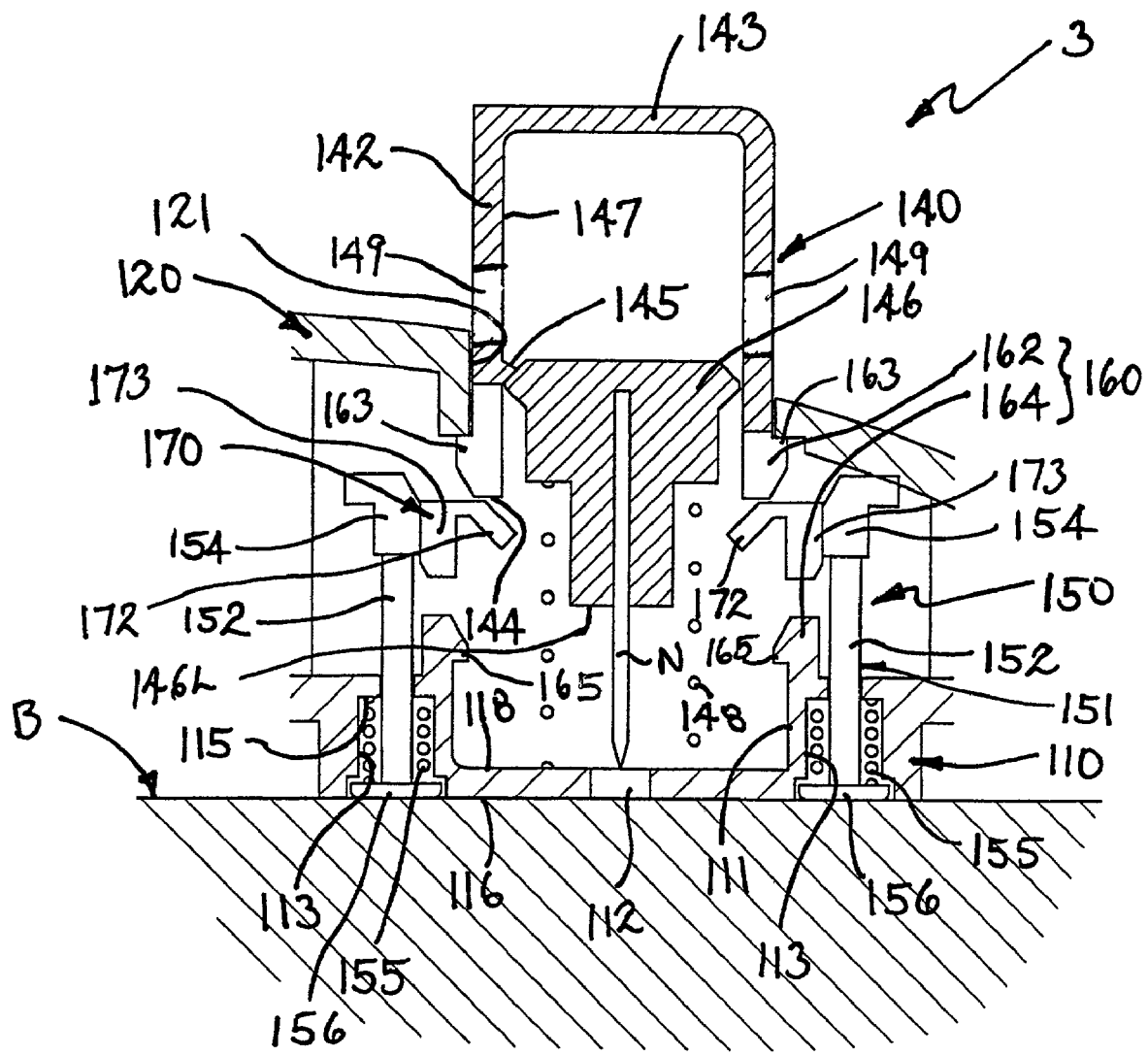
FIG. 14 schematically illustrates a cross-sectional view of a third embodiment of the needle retraction device according to the present invention, where the needle is in a stowed, ready-to-use position.
Figure 15:
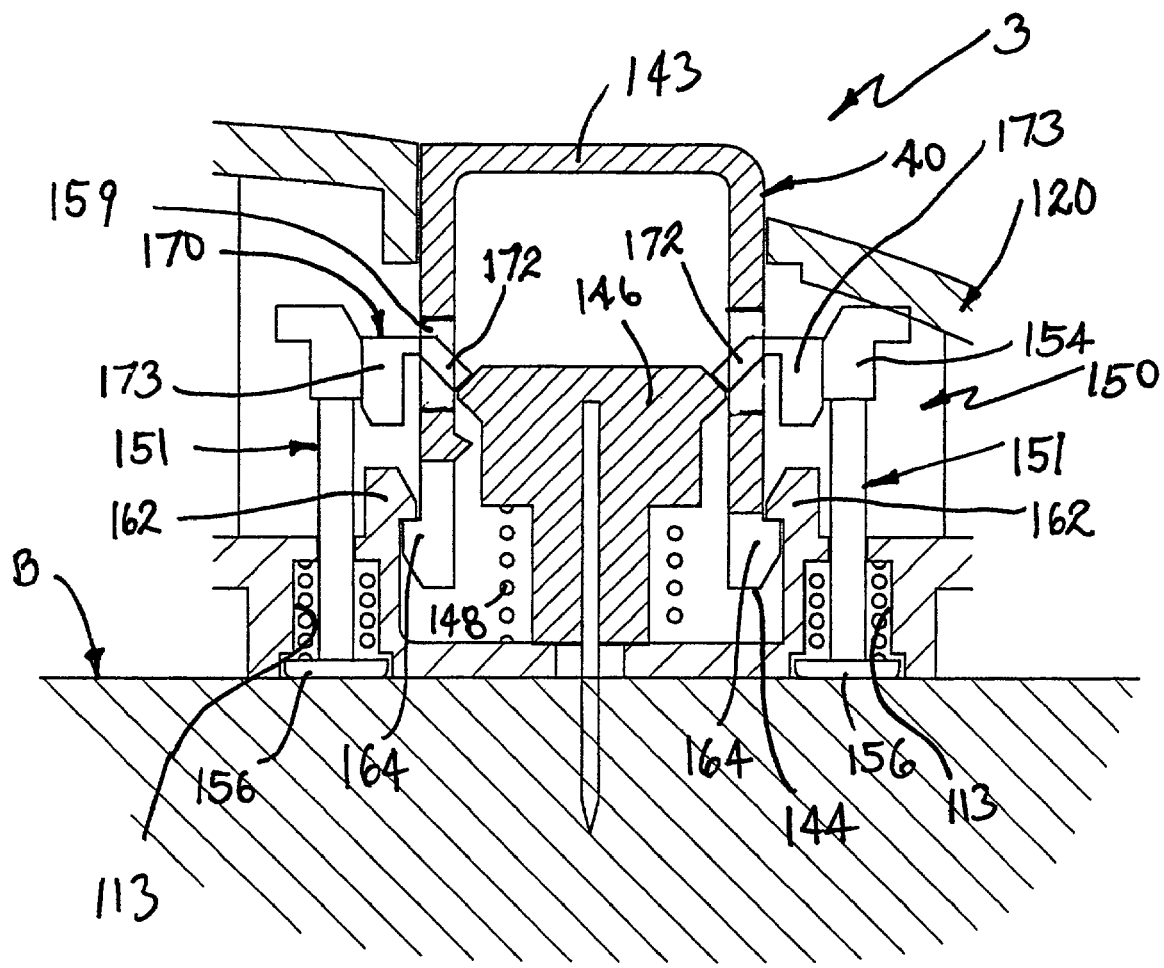
FIG. 15 schematically illustrates a cross-sectional view of the needle retraction device of FIG. 14, where the needle is in the actuated position, penetrating through the skin of a patient's body.
Figure 16:
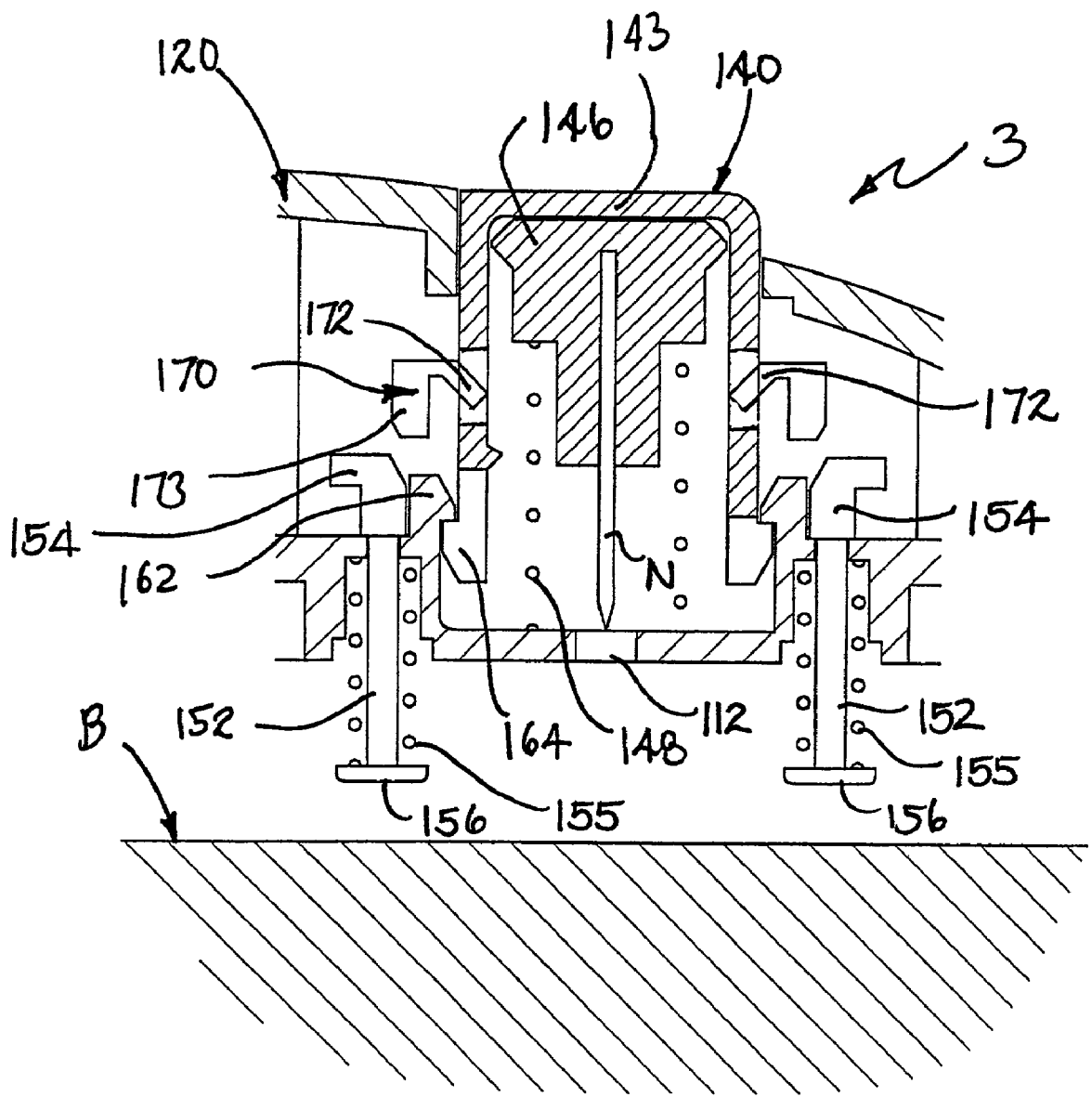
FIG. 16 schematically illustrates a cross-sectional view of the needle retraction device of FIG. 14, but with the needle automatically moved to the retracted position.

FIGS. 14-16 illustrate the third embodiment 3 of the needle retraction device 3 according to the present invention. The third embodiment of the needle retraction device 3 comprises a base 110 and a housing 120, an actuator 140 mechanically associated with a needle N for actuating the needle, a retraction mechanism 150 for withdrawing the needle N, similar to the first 1 and second 2 embodiments.

The base 110 has a through hole 112 aligned with the needle N. As in the first and second embodiments, the base 110 can have an attaching mechanism or system that secures the retraction device 3 to the surface of the patient's skin for a prolonged period. The attaching mechanism, for instance, can be an adhesive layer (not shown) provided on a lower surface 116 of the base 110. The through hole 112 can also extend through the adhesive layer. The adhesive layer can be covered with a protective layer (not shown), which also covers the through hole 112. Alternatively, the attaching device can be a strap, tape, band, or the like, as previously described with the first and second embodiments.

The actuator 140 is movably mounted to the housing 120 and biased upwardly relative to the base 110 using a compression spring 148, similar to the first and second embodiments. The housing 120 has an opening 121 through which the actuator 140 can be movably received and guided downwardly. The opening 121 for the actuator 140 can be any suitable shape, such as circular, square, etc. The actuator 140 includes a depression member 142 formed, for example, of a cylindrical hollow body, e.g., a cup-like body, having a closed top end 143 and an open bottom 144. A needle holder 146 is movably positioned in the housing 110 and dimensioned to be inserted into the depression member 142.

The delivery needle N is connected to the needle holder 146, which has a port (not shown) for delivering medication to the needle N, similar to the first embodiment 1 and second embodiment 2. In this respect, the depression member 142 can have a slot (not shown) for allowing the port to slide relative to the depression member 142. The alignment of the needle N is relatively perpendicular to the through hole 112 located in the base 110. Depressing the depression member 142 lowers the needle holder 146 so that the needle N can penetrate into the body B, as shown in FIG. 15. The depression member 142 has a stop 145 extending substantially radially inwardly from its inner wall 147 (see FIG. 14). The stop 145, which abuts against the upper end of the needle holder 146 along surface 146a, pushes the needle holder 146 down. The needle N becomes fully pushed in, as shown in FIG. 15, when the lower end 146L of the needle holder 146 abuts the upper surface 118 of the base 110. When the needle N is in this position, the stop 145 is forced past the surface 146a of the upper end of the needle holder 146 as the depression member 142 is being pushed, until the depression member 142 is locked to the base 110. In this respect, the device 3 has a first or one-way latch lock 160 for locking the depression member 142 to the base 110, and a second or hold down lock 170 for maintaining the needle holder 146 in the injection position (shown in FIG. 15).

The first lock 160 comprises a one-way lock for locking the depression member 142 in the pushed or depressed position (FIG. 15). The second lock 170 releasably maintains the needle holder 146 in the injection position (FIG. 15) until the needle N is withdrawn by pulling the device 3 away from the patient. The first lock 160 comprises a first lock member 162 formed on the outer periphery of the lower end 144 of the depression member 142 and a complementary second lock member 164 formed on the base 110. The first and second lock members 162, 164 can comprise a plurality of latches or hooks, a continuous latch or hook, or a combination of both. When the first and second lock members 162, 164 engage, they are latched together, as shown in FIGS. 15 and 16. The first and second lock members 162, 164, for example, can be formed respectively by an outwardly extending flange 163 formed circumferentially around the lower end 144 of the depression member 142 and an inwardly extending flange 165 formed circumferentially around a portion of the base 110, collinearly aligned with the depression member 142. Each flange 163, 165 may be continuous or formed at intervals. Alternatively, one of the flange 163 formed on the depression member 142 and the flange 165 formed in the base 110 can be a continuous flange, while the other of the flanges 163, 165 can be formed at intervals, forming at least two points from which the flanges 163, 165 can be latched against.

The base 110 can have an upright wall or walls 111 extending upwardly from the upper surface 118 thereof. The second lock member 164 can be formed at an upper portion of the wall 111. The base 110 also can have a plurality of recesses 113 for slidably accommodating the retraction mechanism 150, namely the plurality of trigger members 151, which extend through the base 110.

The second lock 170 comprises a plurality of projections 172 mounted relative to the base 110 or housing 120, or both. The projections 172 are insertable through the depression member 142 and are biased to move outwardly away from the depression member 142. In this respect, an expandable C-ring 173 or the like, conforming in outer peripheral shape of the depression member 142 and having two or more equally spaced projections 172, can be expandably and retractably mounted to the housing 110, i.e., the ring 173 can expand and contract away and toward the depression member 142, while the C-ring 173 is restrained from vertically moving, such as using abutments or the like (not shown). The depression member 142 can include slots or openings 149 or the like, extending through its wall, to allow the projections 172 to extend therethrough and engage the upper end of the needle holder 146. See FIGS. 15-16. The projections 172 can be hooks or latches, or the like.

The retraction mechanism 150 includes at least one trigger member 151 engageable with the second lock 170 and the skin surface of the body B to maintain the needle holder 146 in the injection position, without having to manually hold down the depression member 142. The retraction mechanism 150 releases the needle holder 146 to retract the needle N when the trigger member 151 looses contact with the body B. In the preferred third embodiment, the device 3 uses a plurality of trigger members 151, such as four (two shown in the cross-sectional view in FIGS. 14-16. Each member is movably mounted to the base 110 and each comprises a rod or leg 152 having a first portion 154 engageable with the second lock 170 and a second portion or foot 156 engageable with the body B. Each leg 152 is slidably mounted to the base 110 and has a compression spring 155 confined in the respective recess 113, between the second portion 156 and the opposing wall 115 formed in the recess 113. The spring 155 biases the associated leg 152 outwardly toward the body B. The second portion 156 has a planar body contact surface to help to compress the spring 90 while the needle retraction device 3 is attached to the body B.

In operation of the third embodiment 3, referring to FIGS. 14-16, the needle retraction device 3 is positioned over a patient's injection site, as shown in FIG. 14, for example, by adhering an adhesive layer (not shown) formed on the bottom surface 116 of the base 110 to the skin surface B. In the ready-to-use state, the depression member 142 is fully extended upwardly and the needle N is in its stowed position, safely within housing 120 and the base 110. Once the device 3 is secured to the skin surface of the body B, the user depresses the depression member 142 until it is fully pressed down so that the first lock 160 permanently locks the depression member 142 to the base 110.

Depressing the depression member 142 immediately moves the needle holder 146 downwardly. As the needle N is being inserted into the body B, the lower end 144 of the depression member 142 or the first lock member 162 pushes the second lock 170 away so that the depression member 142 can be lowered. That is, its lower end 144 pushes the second lock projections 172 outwardly to allow the depression member 142 to move down. When the needle N is fully inserted, as shown in FIG. 15, the stop 145 moves past the upper end of the needle holder 146 to allow the depression member 142 to continue and move downwardly relative to needle holder 146. This causes the first lock member 162 to engage the second lock member 164. At the same time, as the depression member 142 travels in a downwardly direction, the projections 172, are forced into the complementary slots or openings 149 formed through the depression member and engage the upper end of the needle holder 146 as shown in FIG. 15. It should be noted that in this embodiment 3, the outer surface of the projections 172 and the corresponding surface of the needle holder 146 have matingly shaped for effective engagement therewith. The injection position shown in FIG. 15 maintains the needle N in the injection position, while the device 3 remains attached to the body B. In the injection position shown in FIG. 15, the needle N can deliver drug to the user through its port (not shown). This position is held throughout the delivery mode, without having to manually hold down the depression member 142.

Referring to FIG. 16, upon removal of the device 3, away from the skin surface of the body B, the needle N will automatically retract into the housing 120. Specifically, the compressed springs 155 expand to force the trigger members 151 outwardly since the skin surface no longer blocks the foot 156, when the device 3 becomes detached from the body B. That is, the first trigger member portion 154 slides downwardly relative to the second lock ring 173 as the spring 155 propels the foot 156 outwardly. Since the first trigger member portion 154 no longer abut the second lock ring 173, the second lock ring 173 can expand outwardly, moving the second lock projections 172 outwardly to release the needle holder 146. The main compressed spring 148, biasing the needle holder 146 upwardly, forces the projections 172 outwardly, releasing the needle holder 146 and causing the needle holder 146 to move up. The force of the spring 148 pushes the needle holder 146 against the upper closed end 143 of the locked depression member 142 to maintain the needle withdrawn or retracted in the housing 120. Accordingly, the trigger members 151 trigger the release of the second lock 170 to allow safe withdrawal of the needle N.

Fourth Embodiment

FIGS. 17-20C illustrate an embodiment of an automatic needle enveloping device 4 according to another aspect of the present invention. Similar to the first three embodiments described above, the automatic needle enveloping device 4 can be used to deliver medication or fluids to a patient with a needle N or alternative penetrating member to penetrate through the skin and deliver drug or medication to a patient. According this aspect of the invention, the needle N is automatically shielded, safely in a shield immediately upon disengaging the device 4 from the body B. Accordingly, there is no need for the user to discern about manually having to shield the needle N.

The automatic needle enveloping device 4 comprises a housing 220 with a base 210, a first actuator 240, a second actuator 260 mechanically associated with a needle N for actuating the needle N, and a needle enveloping mechanism 230 for shrouding the needle N.

The housing 220 comprises a substantially hollow body 222 having an upper opening 223, a lower opening 224, and a side opening 225. The base 210, which can be integrally formed with the housing 220 at its bottom end, can be substantially flat and sized to abut against the patient's skin surface of the body B. The lower opening 224 is formed through the base 210. A ring 212 or the like protrudes slightly from its bottom surface, forming a recess 214 surrounding the opening 224 and the needle injection site. The upper, lower, and side openings 223, 224, 225 are respectively dimensioned to allow passage of the second actuator 260, a component (shield) of the needle enveloping device 230, and the first actuator 240. Unlike the first three embodiments 1-3, the needle enveloping device 4 is designed to be manually held against the patient's body, without using any attaching or adhering device.

Figure 17:
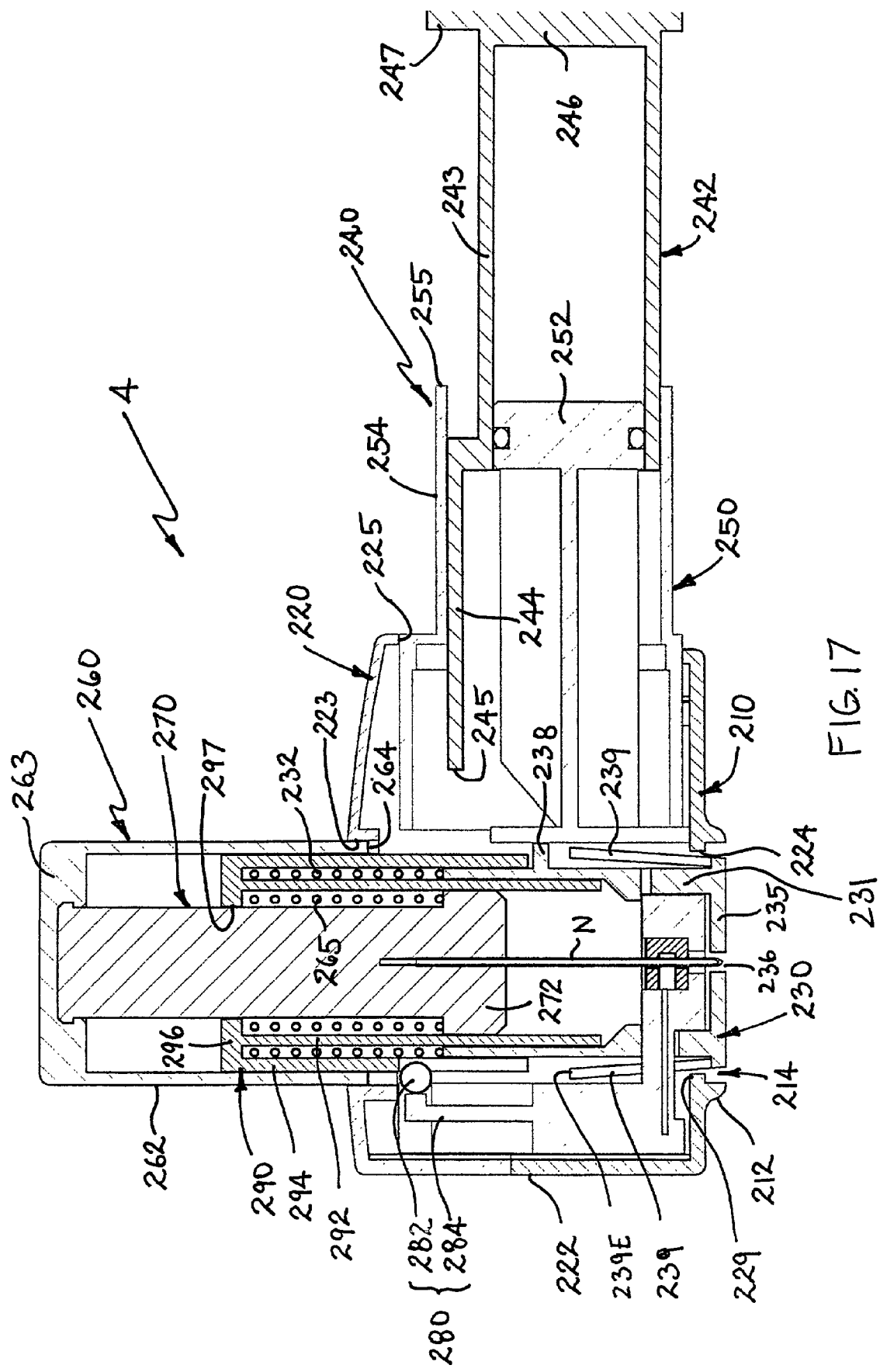
FIG. 17 schematically illustrates a cross-sectional view of an embodiment of a needle enveloping device according to yet another aspect of the present invention, where the needle is in a stowed and locked position.
Figure 18:
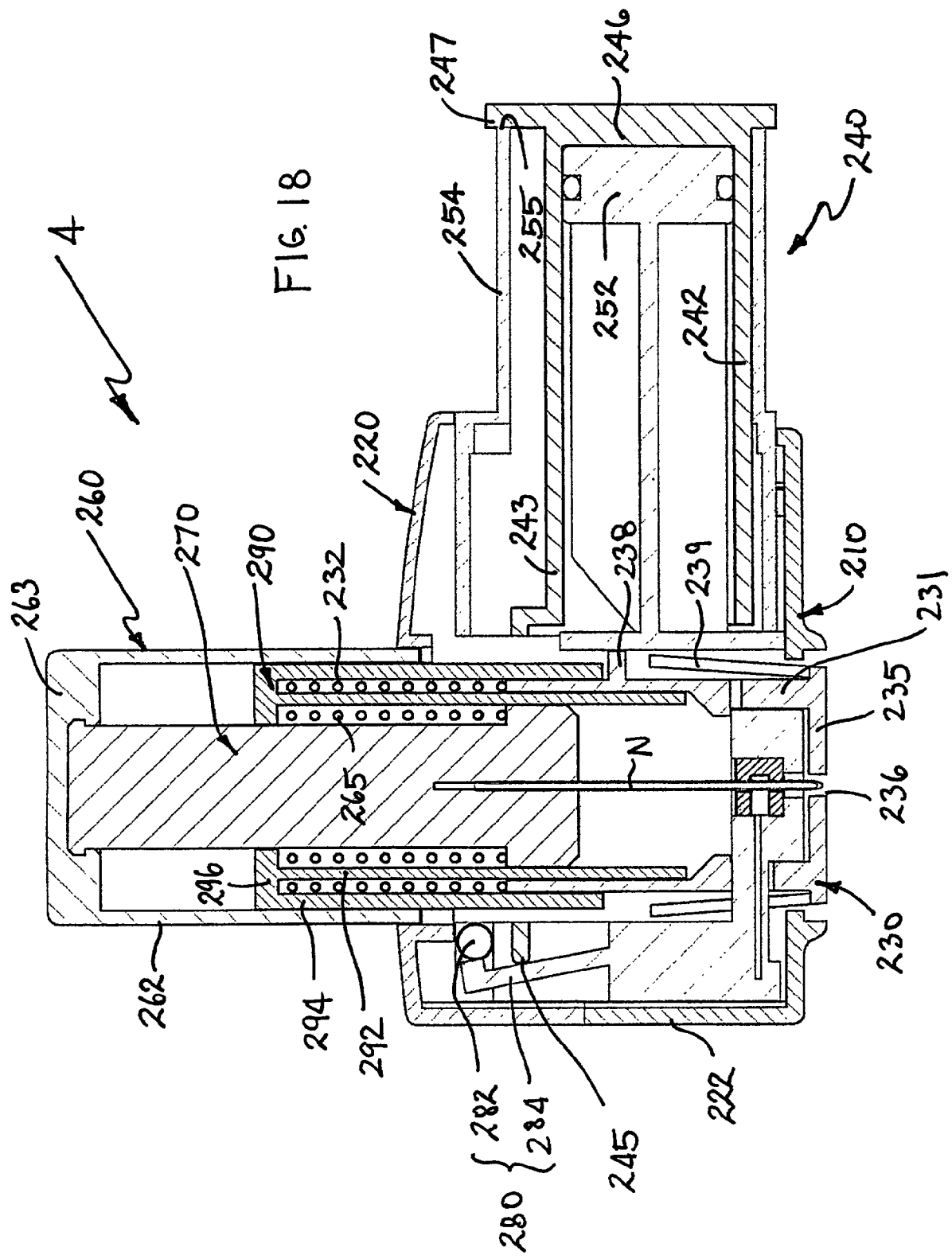
FIG. 18 schematically illustrates a cross-sectional view of the needle enveloping device of FIG. 17, but with its first actuator engaged, placing the needle in the ready to use position.
Figure 19:
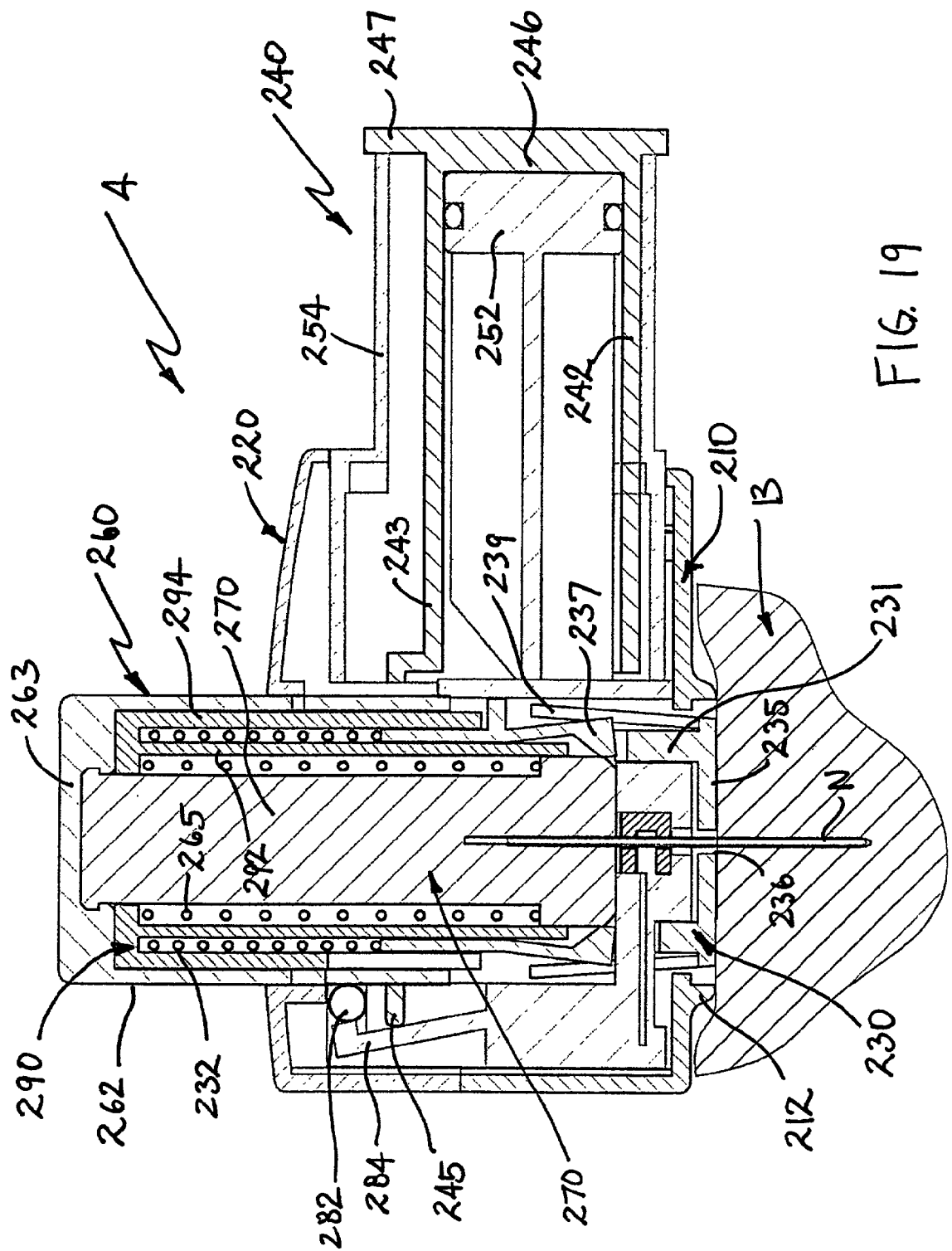
FIG. 19 schematically illustrates a cross-sectional view of the needle enveloping device of FIG. 17, where its second actuator is actuated so that the needle penetrates through the skin of a patient's body.
Figure 20:
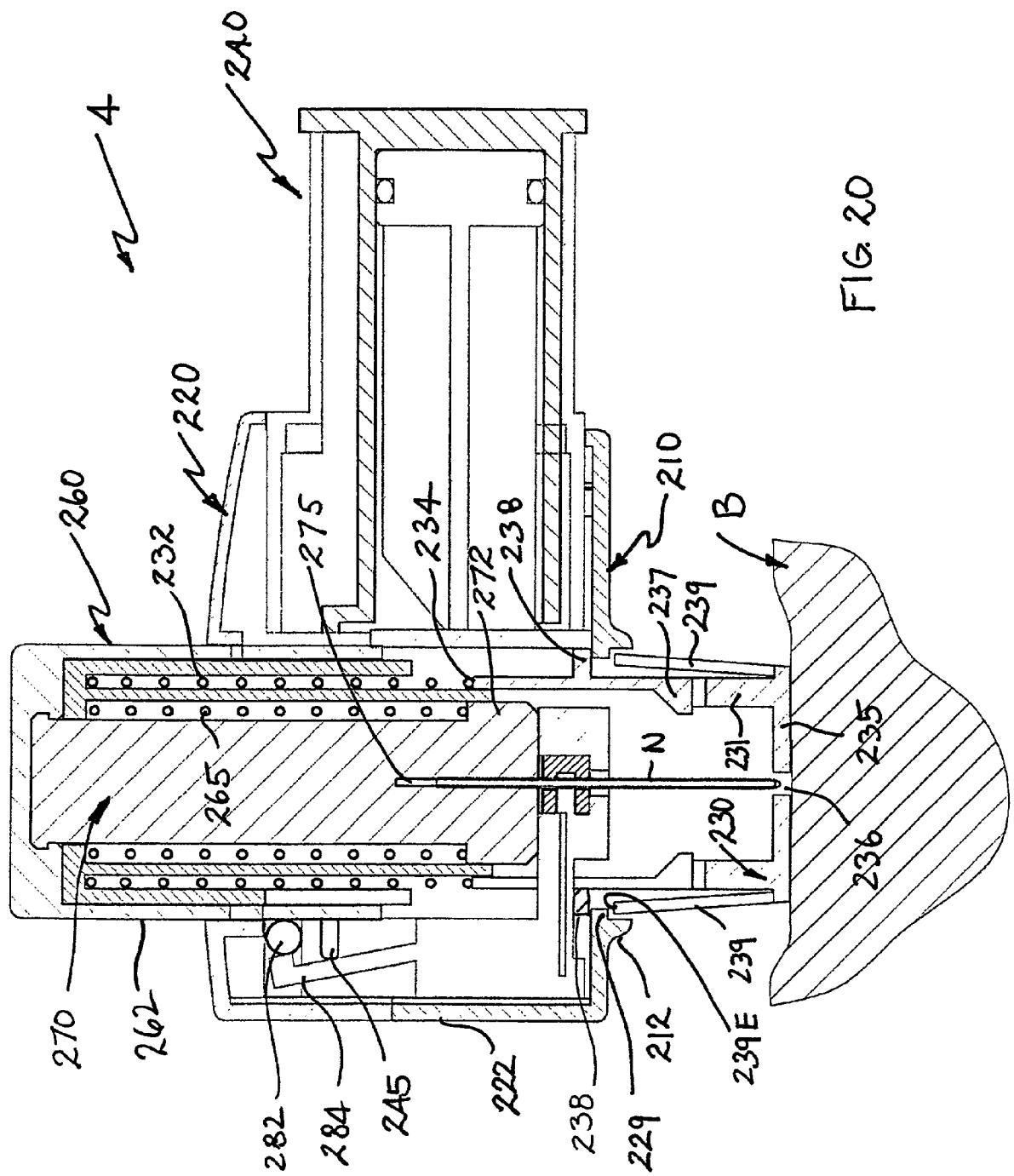
FIG. 20 schematically illustrates a cross-sectional view of the needle enveloping device of FIG. 17, where a needle shield is automatically extended outwardly to shroud the needle.

The first actuator 240 acts as a key to unlock the second actuator 260. Specifically, the first actuator 240 comprises an elongated moving member 242 slidably movable horizontally (relative to the housing 220) from an extended or locked position (FIG. 17) to a retracted or unlocked position (FIGS. 18-20). The first actuator 240 further includes a guide 250, which can comprise a plunger 252 and an outer sleeve 254 non-movably connected to the housing 220. The guide sleeve 254 and the plunger 252 are fixedly attached to the housing 220 and extend through the side opening 225 of the housing 220. The moving member 242 comprises an axially extending hollow portion 243 and an engaging portion 244 extending inwardly from the hollow portion 243. The distal end 245 of the engaging portion 244 is adapted to unlock the second actuator 260 when the moving member 242 is fully pushed in (retracted position), as shown in FIG. 18. The hollow portion 243 receives the plunger portion 252, which guides the moving member 242. When the plunger 252 abuts against the proximal end 256 of the moving member 242, the first actuator 240 is in the retracted position, as shown in FIG. 18. Moreover, the proximal end 246 can also include a flange 247 that can abut against a proximal end 255 of the outer sleeve 254, as shown in FIGS. 18-20.

Figure 20A:
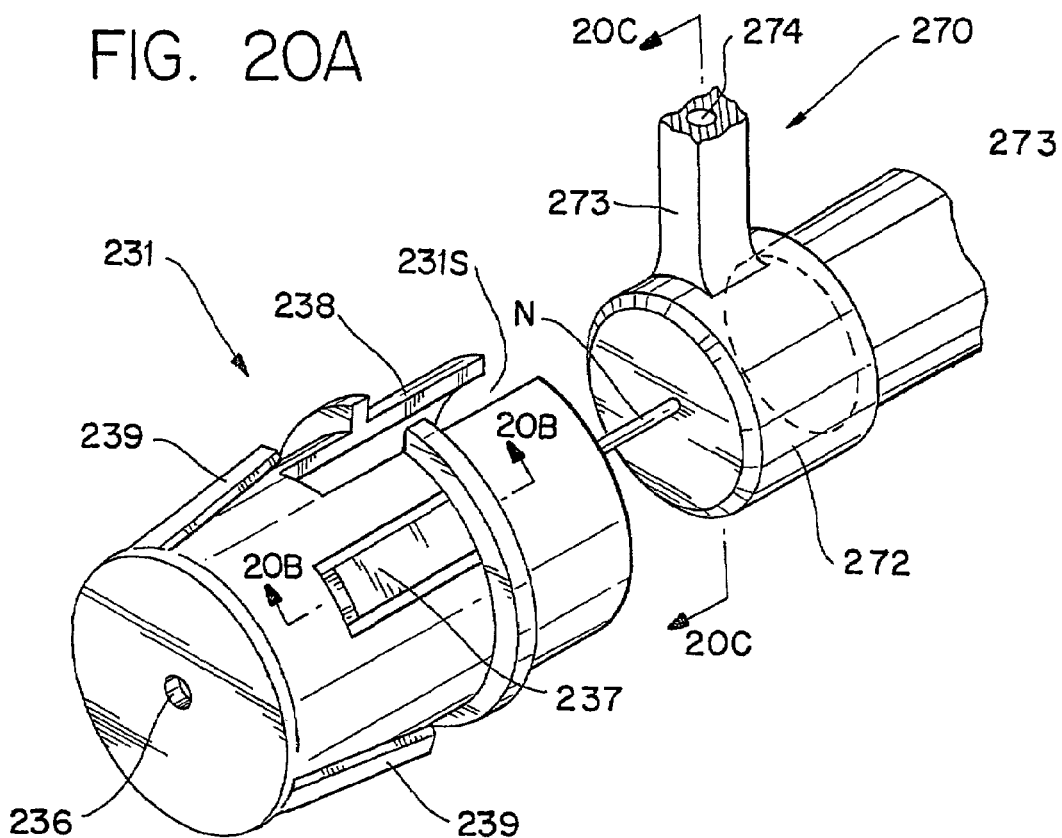
FIG. 20A schematically illustrates an exploded view of the components of the needle enveloping device of FIG. 17.
Figure 20B:
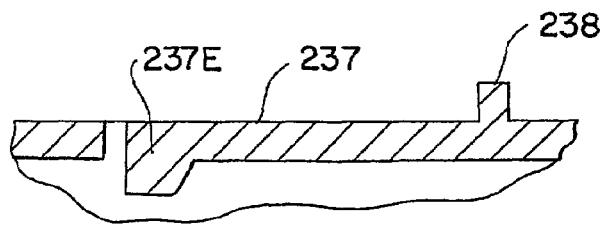
FIG. 20B illustrates a cross-sectional view taken along line 20B-20B of FIG. 20A.
Figure 20C:
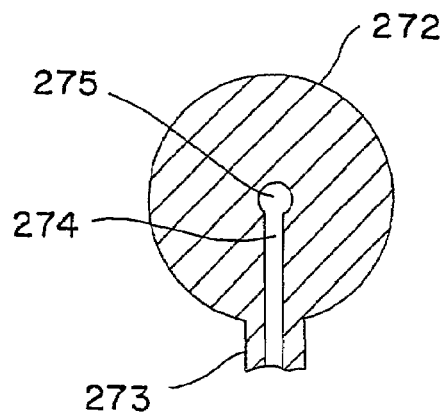
FIG. 20C illustrates a cross-sectional view taken along line 20C-20C of FIG. 20A.

The second actuator 260 comprises a substantially cylindrical body 262 connected to the needle N. The body 262 further includes a needle holder 270 fixedly connected to the closed upper end 263 of the body 262. The needle holder 270 extends downwardly toward the lower end 264 of the body 262, concentric with the body 262 and the needle N, which is fixedly attached to the lower end of the needle holder 270. Referring to FIGS. 20A and 20C, the needle holder has a drug delivery port 274 that communicates with the needle chamber 275. The port 274 is formed through an arm 273 that extends radially from an enlarged flange portion 272 of the needle holder 270. The actuator body 262 is movably mounted to the housing between an extended (unactuated) position (FIGS. 17-18) and a depressed (actuated) position (FIGS. 19-20). A first compression spring 265 is positioned within the actuator body 262 to bias the same to the depressed position.

To lock the actuator body 262 at its extended position, the second actuator 260 has a lock 280, which can comprise a ball 282 positioned in the path of the actuator body 262. Specifically, the ball 282 is positioned to abut the lower end 264 of the actuator body 262 and prevent the actuator 260 from being actuated, i.e., lowered. See FIG. 17. To maintain the ball 282 in the path of the actuator body 262 at all times, a retainer 284 is positioned to abut against the ball 282. The retainer 284 can be fixedly attached to the housing 220. When the first actuator 240 is moved to the retracted position (FIGS. 18-20), its engaging portion 244 pushes the retainer 284, bending or flexing the same away from the ball 282, as shown in FIGS. 18-20. The ball is not free to move away when the device 4 is tilted or positioned vertically, i.e., positioning the device so that the actuator body 262 is substantially horizontal. The engaging portion 244 is "forked" so that it bypasses around the actuator body 262, and the retainer 284 is wide enough to intercept the distal ends 245 of the engaging portion. Specifically, the engaging portion 244 can be substantially U-shaped having a pair of arms that can move across the outer sides of the actuator body 262. A pair of distal ends 245 can push against the retainer 284. This allows the ball 282 to move away from the path of the actuator body 262 when the device 4 is tilted or oriented vertically as previously explained, which allows as the second actuator 260 to be lowered to its actuated position. Thus, a double action, unlocking the second actuator 260 and tilting the device 4, is required to actuate the second actuator for added safety.

The second actuator 260 further includes a sleeve member 290 fixedly connected to the housing 220. The sleeve member 290 has a first sleeve 292 and a second sleeve 294 positioned outside the first sleeve 292. The first and second sleeves 292, 294 are concentrically connected together with an end member 296. The end member 296 has a central opening 297 through which the needle holder 270 extends. The enlarged lower flange portion 272 is dimensioned to slide against the inner wall surface of the first sleeve 292, as shown in FIGS. 17 and 18. The first spring 265 is positioned between the needle holder 270 and the first sleeve 292, with the spring ends abutting the flange portion 272 and the end member 296. In this respect, referring to FIG. 17, the spring 265 is under compression when the actuator body 262 is in the extended position. The compression is released when the actuator body 262 is depressed, as shown in FIG. 19. Thus, the actuator body 262 is biased toward the depressed position shown in FIG. 19. There are a number of ways to maintain the actuator 260 in the extended position (FIG. 17) against the downwardly exerting force of the first spring 265. For instance, actuator body 262 can be attached to the housing 220 using frangible (break away) elements (not shown), or the housing 220 and the actuator body 262 can have a detent or stop (not shown) arranged so that the actuator 260 can only be pushed down to the actuated position by overcoming the detent or stop. More specifically, the detent or stop can be arranged so that the user would need to twist or rotate the actuator body 262 to release the detent or stop. The user can twist the actuator body 262 from the housing if frangible elements are used. The detent or stop also can be arranged so that pushing the actuator body 262 past the detent or stop by a manual force overcomes the same to allow the actuator 260 to move down. In any event, once the actuator 260 is released from the constraint of the detent, stop, frangible elements, etc., the first spring 265 takes control in moving the actuator to the actuated position.

Referring to FIG. 20, the needle enveloping mechanism 230 comprises a needle shield 231 and a second spring 232. The needle shield 231 is a substantially hollow body with an open upper end 234 and a closed lower end 235, with an opening 236 to permit passage of the needle N. The needle shield 231 is configured to slide between the first and second sleeves 292, 294, and movable between a retracted position (FIGS. 17-19) and an extended position (FIG. 20). The second spring 232 is positioned between the first and second sleeves 292, 294, with the spring ends thereof abutting the end member 296 and the upper end 234 of the needle shield 231. In this respect, referring to FIG. 17, the spring 232 is compressed at all times, except when the needle shield 231 is extended. The compression is released when both the actuator body 262 is depressed and the device 4 is moved away from the patient's body B. Thus, the needle shield 152 is biased to rove toward the extended position shown in FIG. 20 when the second actuator 260 is pushed in to its retracted position shown in FIGS. 19-20.

Referring to FIG. 19, the needle shield 231 is held connected to the sleeve member 290, which is fixed relative to the housing 220, against the downwardly urging force of the second spring 232. To enable or activate the needle shield 231 to move, the shield 231 has a plurality of tabs or latches 237 that can be moved outwardly as the second actuator 260 is actuated, i.e., pushed down. Specifically, as the needle holder 270 moves down with the actuator body 262, the lower end of the needle holder 270 or its flange 272 abuts against the latches 237 and pushes the latches 237 outwardly to activate the needle shield 231. Referring to FIGS. 20A and 20B, the shield 231 has at least two latches 237 suspending from the first stop 238, which is outwardly extending annular flange. In this respect, the latches 237 are cantilevered so that their free end portion 237E (FIG. 20B) can flex outwardly. For instance, the latches 237 each can comprise a thin strip of material that can flex outwardly as shown in FIG. 19. The latches 237 are attached to the first sleeve 292 using, for instance, adhesive, frangible members, etc. Outwardly forcing the latches 237 as shown in FIG. 19 breaks away the needle shield 231 from the fixed sleeve member 290 to allow the needle shield to move down by the biasing force of the spring 232 as the device 4 is lifted off the patient's body B. The spring 232 automatically pushes the shield 231 outwardly once the latches 237 are broken away from the sleeve member 290.

The shield 231 can further include second stop 239. The first and second stops 238, 239 limit and lock the shield 231 after it is moved to its extended position, as shown in FIG. 20. The first stop 238 can abut against the peripheral edge 229 of the lower opening 224 formed in the base 210 to limit the outward extension. The second stop 239 can be a plurality of one way latches or the like that allow sliding of the shield 231 in one (extended) direction, but not in reverse. Referring to FIG. 20, the latches 239 are configured so that they expand once they pass through the lower opening 224. Once expanded, the latch ends 239E can abut against the peripheral edge 229 of the lower opening 224 to prevent the shield 231 from being retracted. As the shield 231 is locked in place, the device 4 is rendered inoperative.

To accommodate the relative movement of the flange portion 272 with the port arm 273 relative to the sleeve member 290 and the shield 231, the first and second sleeves 292, 294 each have a slot (not shown) dimensioned to pass the port arm 273. Similarly, the shield 231 has a slot 231S to accommodate the port arm 273.

In operation of the needle enveloping device 4, referring to FIGS. 17-20, the needle enveloping device 4 is positioned so that the lower end of the shield 231 contacts the skin of the body, as shown in FIG. 19. The first and second actuators 240, 260 are in the fully extended position, with the needle N in its stowed position, safely within housing 220, as shown in FIG. 17. Just before using the device 4, the user depresses the moving member 242 (first actuator 240) to unlock the second actuator by moving the retainer 284 away from the locking ball 282. The second actuator 260 can be actuated by tilting the device 4 vertically, where the actuator body 262 is moved toward horizontally, while the moving member 242 is situated vertically (above) so that the ball 282 can fall down out of the way of the actuator body's pathway.

The user holds the device 4 to the skin surface of the body B while the device 4 is tilted or vertically oriented as described above, and depresses (or rotates) the actuator body 262 to free the actuator body 262 relative to the housing 220. Once the actuator body 262 is unrestrained from the housing 220, the spring 232 takes control and immediately propels the actuator 260, including the needle holder 270 with the needle N, downwardly. When the needle N is inserted into the body B (FIG. 19), the lower end of the needle holder 270 or its flange 272 pushes the latches 237 outwardly to activate the needle shield 231. This breaks away the needle shield 231 from the fixed sleeve member 290 to allow the needle shield to move outwardly by the force of the spring 232 as the device 4 is lifted off the patient's body B.

When the needle N is fully inserted, as shown in FIG. 19, the needle N can deliver drug to the user through its port 273. This position is manually held throughout the delivery mode.

Referring to FIG. 20, upon releasing the device 4 away from the surface skin of the body B, the needle shield 231 will automatically extend out to cover the needle N. Specifically, the spring 232 forces the shield 231 outwardly, when the device 4 is moved away from the body B. Once the shield 231 is extended outwardly, it is locked in this position with the latches 239.

Fifth Embodiment

FIGS. 21-23 schematically illustrate another embodiment of a needle retraction device according to yet another aspect of the present invention. In this embodiment, the automatic needle retraction device 5 includes a slidable cover 322 that permanently blocks a needle passage opening 334 to prevent reuse. The needle retraction device 5 comprises an actuator 310 holding a needle N, a retraction assembly 320, and a housing 330 containing the actuator and the retraction assembly. The housing 330 has a base 332 with the needle opening 334 for passage of the needle N. The actuator 310 is vertically movably guided in the housing so that it can move up and down, as shown in FIGS. 21-23. The actuator 310 can be constrained to move vertically using any conventional means, such as a vertical I-shaped slot and a pin (both not illustrated).

Figure 21A:
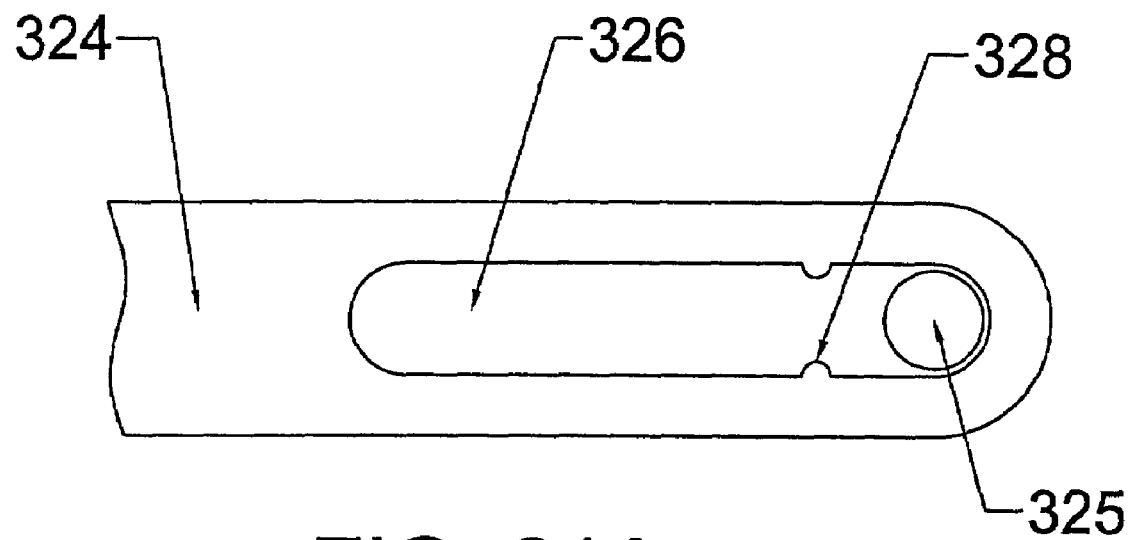
FIG. 21A schematically illustrates an exploded view of the linkage of the needle retraction device of FIG. 21.

The retraction assembly 320 comprises a base or cover member 322 and at least one linkage 324, a pair of opposing and parallel linkages 324 (only one shown) being preferable. The linkages 324 can be pivotally connected to the sides of the actuator 310 by a pin or pins 325 and can be pivotally connected the sides of the base member 322 also using a pin or pins 327. The linkages 324 each have a slot 326 extending axially therealong. The linkages 324 can be biased to move the actuator 310 toward the retracted position (FIG. 21) using a spring or the like (not shown). Each slot 326 is configured so that the respective pin 325 engaging the slot 326 do not allow the linkages 324 to return to its original position (abutting the proximal end of the slot 326 as shown in FIG. 21). In this respect, the slot can have a detent 328 or the like, such as a neck portion or bumps that create a width smaller than the diameter of the pin 325. See FIG. 21A. The manual downward force of the actuator 310 is sufficiently great to force the pins 325 past the detent 328, but the spring biasing force that urges the actuator 310 upwardly is insufficient to clear the detent 328. In essence, the length of the slot 326 is shortened once the actuator 310 is moved down (i.e., when the pin 325 move past the detent 328). For the linkage 324 to enable the actuator 310 to return to its original position (FIG. 21), to make up for the slot length loss, the linkage 324 itself has to move or shift. In this respect, as the base member 322 is slidably mounted to the base 332, the linkage 324 will force the base member 322 inwardly to make up for the slot length decrease. When the base member 322 is moved inwardly, it slides past the needle opening 334 to cover the opening 334.

In operation, referring to FIGS. 21-23, as the actuator 310 is constrained to move vertically as it is being pushed downwardly, the slot 326 enables the linkage 324 to translate or slide relative to the actuator 310 within the confines of the slot 326 as the actuator 310 is being moved down. Once the actuator 310 has been moved down to the needle extended position (FIG. 22), and subsequently released after drug delivery, a spring (not shown) urges the actuator 310 upwardly. Since the slot 326 is configured so that the pin 325 engaging the slot does not allow the linkage 324 to return to its original position, the base member 322, which is slidable, will slide inwardly and cover the opening 334. The thickness of the base member 322 is configured so that the needle tip is close to or abuts it. After the needle is moved to its locked position in FIG. 23, because the needle abuts against cover 234 if the actuator 310 is pushed downwardly, or is abutting it, the base member 322 cannot slide outwardly to uncover the opening 334.

Sixth Embodiment

FIGS. 24-27 schematically illustrate another embodiment of the needle retraction device according to yet another aspect of the present invention. In this embodiment, the automatic needle retraction device 6 includes a needle bending assembly 410 that plastically bends the needle N when it is retracted, to render the device useless after a single use. The needle retraction device 6 comprises the needle bending assembly 410, an actuator 420 holding a needle N, and a housing 430 that contains the actuator 420 and the needle bending assembly 410. Similar to the embodiment of FIGS. 21-23, the housing 430 has a base 432 with a needle opening 434, and the actuator 420 is vertically movably guided in the housing 430 so that it can move up and down, as shown in FIGS. 24-27; the actuator 420 is constrained to move vertically only using any conventional means, such as a vertical slot and a pin (both not illustrated).

Figure 24A:
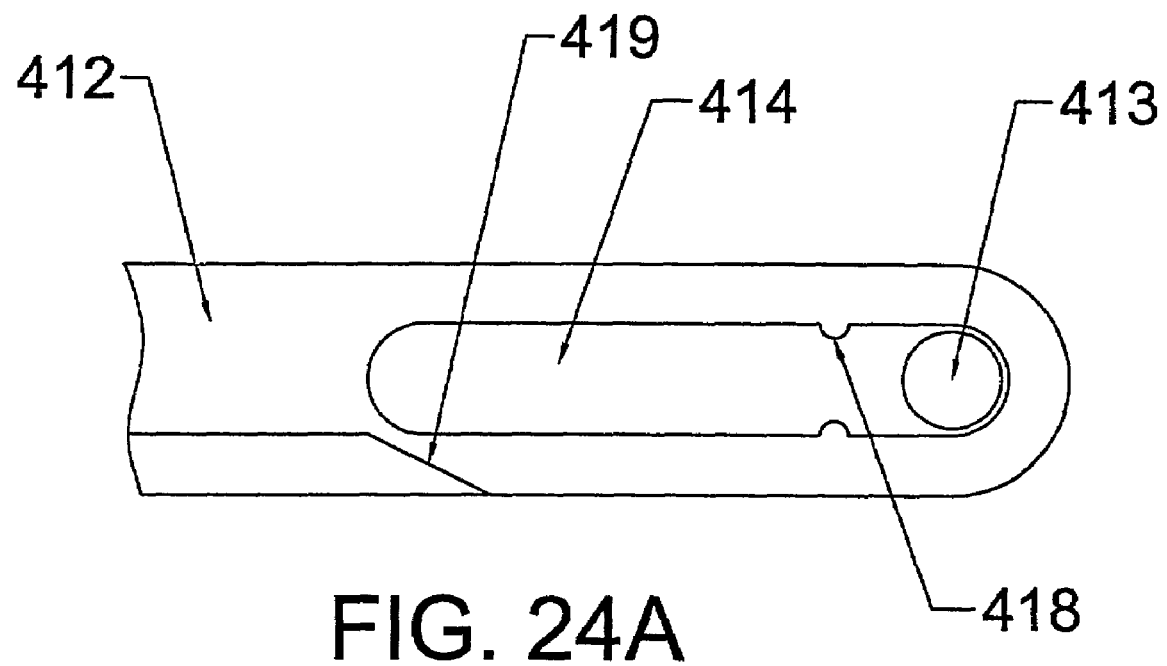
FIG. 24A schematically illustrates an exploded view of the linkage of the needle retraction device of FIG. 24.
Figure 24:
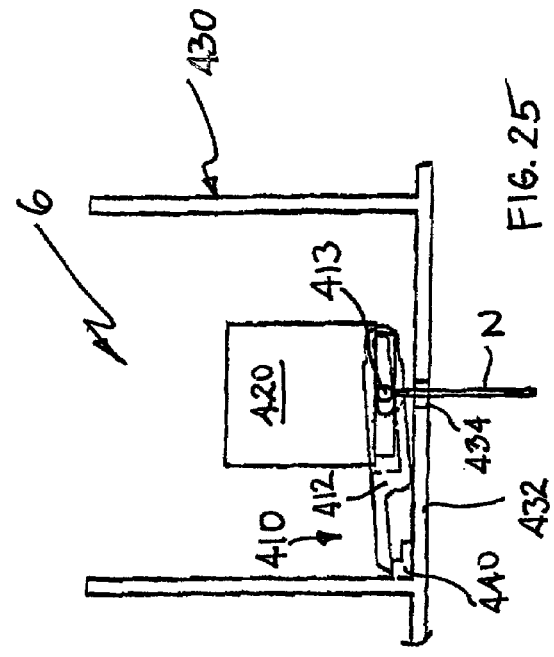
FIG. 24 schematically illustrates a cross-sectional view of yet another embodiment of the needle retraction device according to yet another aspect of the present invention, where the needle is in a stowed, ready to use position.
Figure 25:
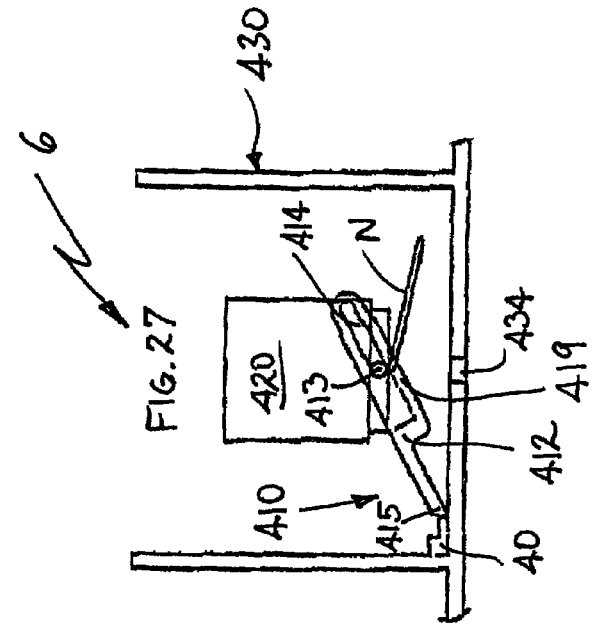
FIG. 25 schematically illustrates a cross-sectional view of the needle device of FIG. 24, but with the needle in the actuated position, where the needle can penetrate through the skin of a patient's body.
Figure 26:
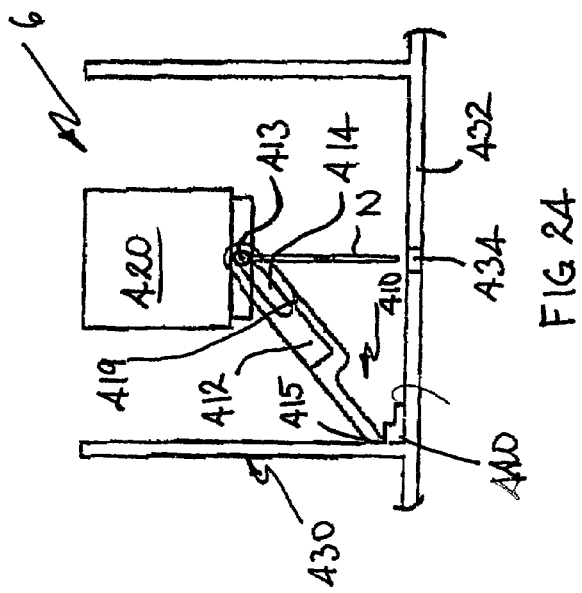
FIG. 26 schematically illustrates a cross-sectional view of the needle retraction device of FIG. 24, but with the needle automatically moved to the retracted position.

The needle bending assembly 410 comprises at least one linkage 412 pivotally connected to one side of the actuator 420 using a pin 413 extending outwardly from the side of the actuator 420. The distal end 415 of the linkage 412 is not fixed so that the linkage 412 can pivot about the pin 413. The linkage 412 has a slot 414 extending axially therealong, similar to the embodiment of FIGS. 21-23. The linkage 412 is biased to move the actuator 420 toward the retracted position (FIG. 24) using a spring or the like (not shown). The slot 414 is configured so that the pin 413 engaging the slot 414 does not allow the linkage 412 to return to its original position, as disclosed in the embodiment of FIGS. 21-23. The manual downward force of the actuator 420 allows the pin 413 to clear the detent 418 (see FIG. 24A), but the spring biasing force that urges the actuator 420 upwardly is insufficient to clear the detent 418. The length of the slot 414 is effectively shortened after the actuator 420 has been lowered. For the linkage 412 to enable the actuator 420 to return to its original position (FIG. 24), the linkage 412 has to move inwardly to make up for the slot length loss. As the distal end 415 of the linkage 412 is free to move, the upward movement of the actuator 420 will rotate the linkage 412 counterclockwise, thus forcing the distal end 415 of the linkage 412 inwardly to make up for the slot distance loss. In this respect, the base 432 is provided with a stepped member 440 having a first abutting portion 442 and a second abutting portion 444.

The linkage 312 further includes a cammed portion 419 (see FIG. 24A) that can engage a portion of the needle N when the linkage is pivoted about the pin 413 to abut the second abutting portion 444. The cammed portion 419 extends inwardly from one side of the actuator 420 toward the needle N. As the cammed portion 419 engages the needle N when the actuator 420 is returned to the retracted position, as soon as one attempts to reactivate the actuator 420, the cammed portion 419 plastically bends the needle N away from the base opening 434 to render the device 6 inoperative, as illustrated in FIG. 27.

Figure 27:
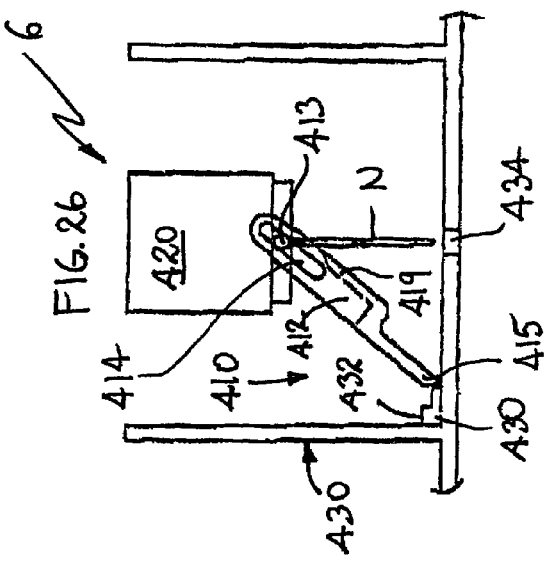
FIG. 27 schematically illustrates a cross-sectional view of the needle retraction device of FIG. 24, but with the needle plastically bent upon re-actuating the needle.

In operation, referring to FIGS. 24-27, as the actuator 420 is constrained to move vertically as it is pushed downwardly, the slot 414 enables the linkage 412 to translate or slide relative to the actuator 420 within the confines of the slot 414 as the actuator 420 is being moved down. Once the actuator 420 has been moved down to the needle extended position (FIG. 25), and released after drug delivery, a spring (not shown) urges the actuator 420 up. Since the slot 414 is configured so that the pin 413 engaging the slot 414 does not allow the linkage 412 to return to its original position, the linkage distal end 415 will drop down from the first abutting portion 442 to the second abutting portion 444 as the linkage is pivoted about the pin 413. When the linkage distal end 415 abuts the second abutting portion 444, the cammed portion 419 engages the needle N and bends it if one attempts to depress the actuator 420, as illustrated in FIG. 27.

Seventh Embodiment

Figure 28:
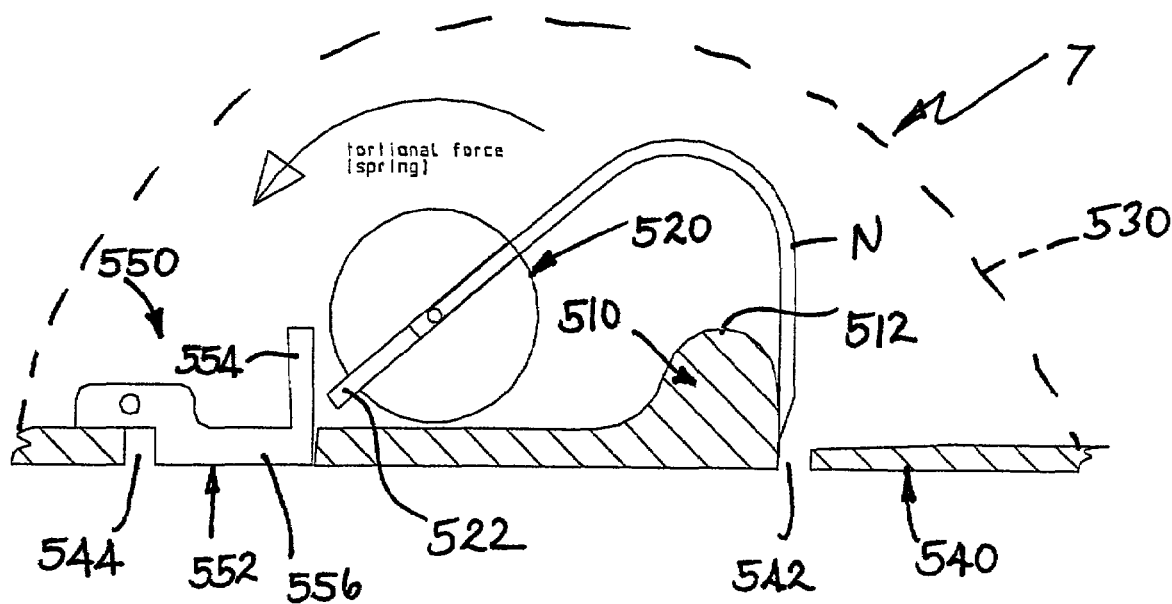
FIG. 28 schematically illustrates a cross-sectional view of yet another embodiment of the needle retraction device according to yet another aspect of the present invention, where the needle is in a stowed, ready to use position.
Figure 29:
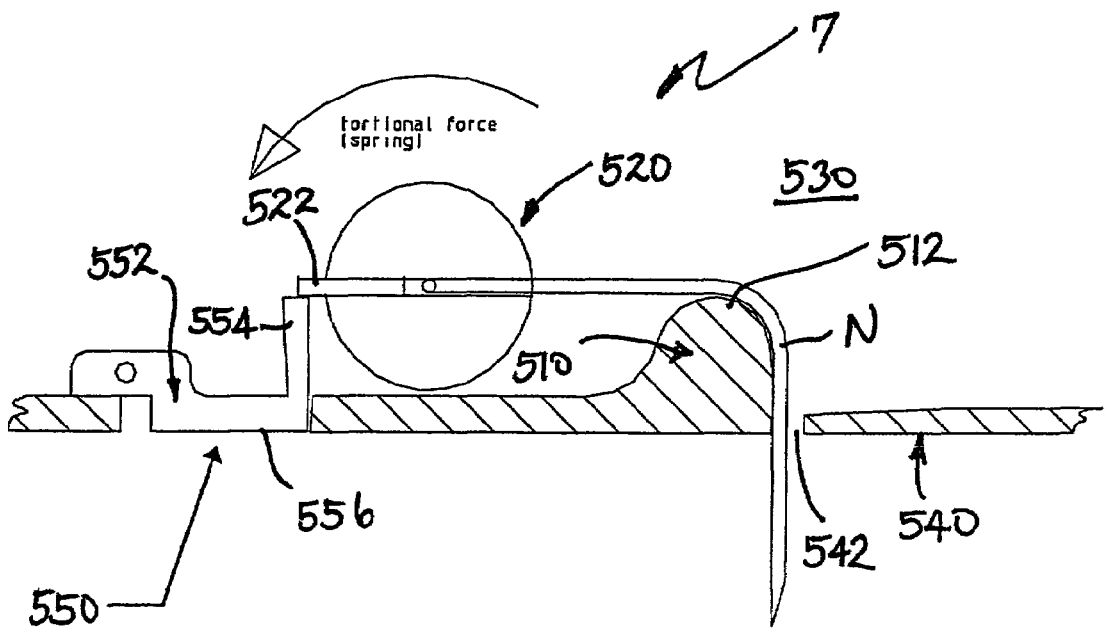
FIG. 29 schematically illustrates a cross-sectional view of the needle device of FIG. 28, but with the needle plastically bent during use, and in the actuated position where the needle can penetrate through the skin of a patient's body.
Figure 30:
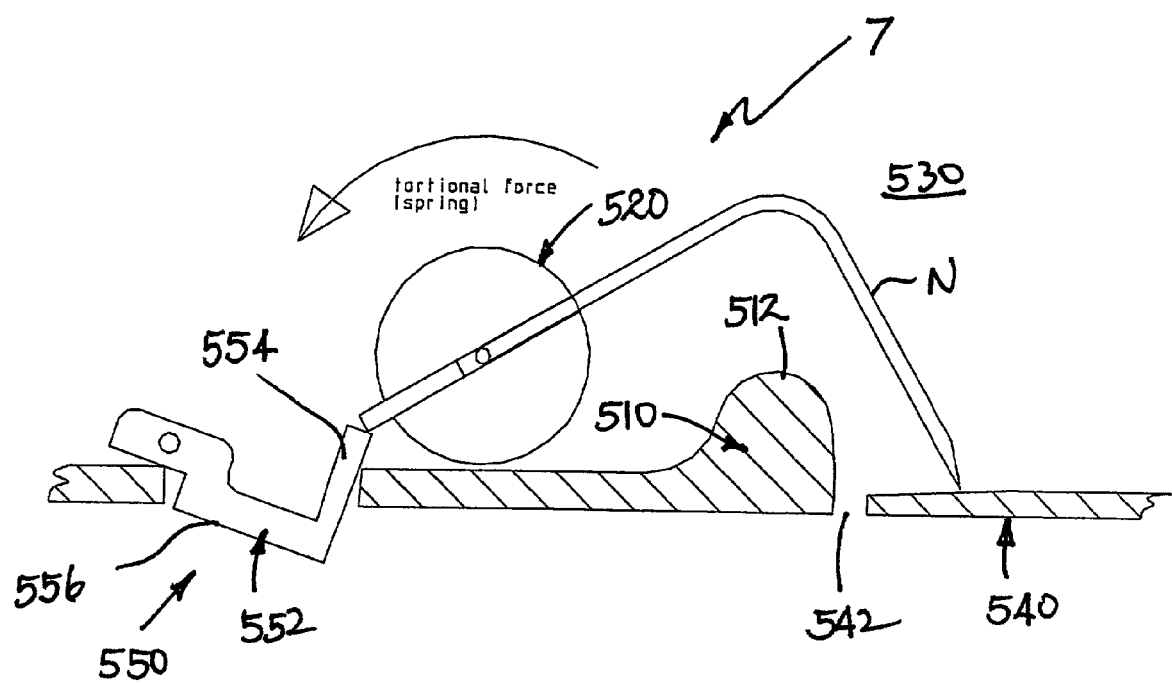
FIG. 30 schematically illustrates a cross-sectional view of the needle retraction device of FIG. 28, but with the needle automatically moved to the retracted position.
Figure 31:
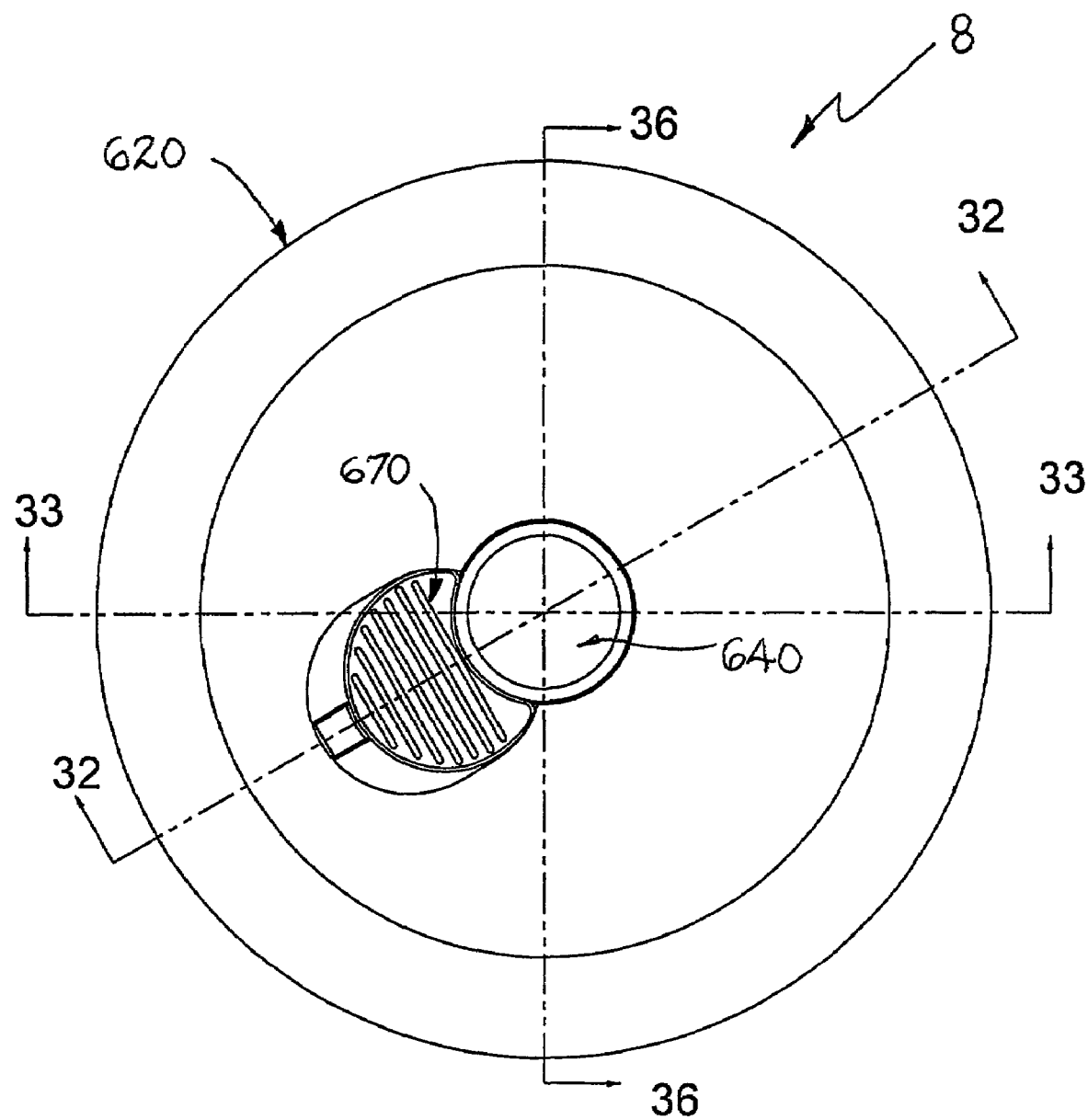
FIG. 31 schematically illustrates a top view of yet another embodiment of the needle-enveloping device according to yet another aspect of the present invention.

FIGS. 28-30 schematically illustrate another embodiment according to yet another aspect of a needle retraction device. In this embodiment, the needle retraction device 7 includes a needle bending assembly 510 that plastically bends the needle N to render the device 7 inoperative after a single use. The needle retraction device 7 comprises the needle bending assembly 510 and a needle actuator 520 holding a needle N, and a housing 530 that contains the actuator and the needle bending assembly.

The housing 530 has a base 540 with a first opening 542 and a second opening 544. As previously disclosed with the first and second embodiments, the base 540 can be substantially flat and flexible to enable the base 540 to adhere to and follow the contour of patient's skin. The first opening 542 is aligned with the needle N and the second opening 544 is aligned with a retraction mechanism 550. The base 540 can have an attaching device (not shown) that secures the retraction device 7 to the surface of the patient's skin for a prolonged period. The attaching device, for instance, can be an adhesive layer provided on a lower surface of the base 540. Alternatively, the attaching device can be a strap, tape, band, or the like (not shown), which allows the patient to secure the device 7 to a desired body site.

The bending assembly 510 has a cam 512 that can be integrally formed with the base 540 and contiguous with the first base opening 542. The needle actuator 520 is rotatably connected to the housing 530 and is spring biased to rotate in the counterclockwise direction (withdrawn position), as shown in FIG. 28. The needle N is pre-bent at an acute angle (less than 90°). When the actuator 520 is rotated clockwise, the bent needle N rides on the cam 512, which is configured to plastically deform the needle to about 90°, as shown in FIG. 29.

The needle retraction mechanism 550 comprises a trigger member 552 pivotally connected to the housing 530. The trigger member 552 has a first portion 554 and a second portion or foot 556. The second portion 556 is adapted to contact the body B and the first portion 554 is adapted to engage the actuator 520, through an extension member 522 that extends outwardly from the actuator 520, when the needle is fully extended (FIG. 29). As the actuator 520 is rotated clockwise to bend and extend the needle N, the extension member 522 is forced past the first portion 554 and abuts it as shown in FIG. 29. The trigger member 552 now prevents the actuator 520 from rotating counterclockwise as long as the second portion 556 engages the body B while the base 540 remains attached to the patient. The second portion 556 extends in the second opening 544 formed in the base 540 to contact the patient and prevent the trigger member 552 from rotating clockwise (FIG. 29). If the base 540 is moved away from the patient, such as when pulling off the device 7 from the patient, since the second portion 456 is not blocked, the spring (not shown), which urges the actuator 520 counterclockwise, forces the trigger member 552 to rotate clockwise (referring to FIG. 30) to automatically retract the actuator 520, and thus the needle N into the housing 530. Because the needle is plastically deformed to about 90°, once the needle N has been withdrawn, as shown in FIG. 30, the point of the needle N is displaced from the opening 542, rendering the device 7 inoperative.

Eighth Embodiment

FIGS. 31-36 illustrate another embodiment of an automatic needle-enveloping device 8 according to another aspect of the present invention. According this aspect of the invention, the needle N is automatically shielded, safely in a shield immediately upon disengaging the device 8 from the body B, similar to the fourth embodiment 4. Accordingly, there is no need for the user to discern about manually having to shield the needle N.

The automatic needle enveloping device 8 comprises a housing 620 with a base 610, an actuator 640 mechanically associated with a needle N for actuating the needle, and a needle enveloping mechanism 630 for shrouding the needle N.

The housing 620 comprises a substantially hollow body 622 having an upper opening 623 and a lower opening 624. A sleeve 621 depends downwardly from the upper opening 623 and has opposing channels (not visible) for accommodating the actuator 640. The base 610, which can be integrally formed with the housing 620 at its bottom end or attached thereto using screws 611 or the like, can be substantially flat and sized so that it can be attached to the skin surface of the body B. The lower opening 624 is formed through the base 610. The base has a recess 614 in its bottom surface surrounding the opening 624. See FIG. 35. The upper and lower openings 623, 624 are respectively dimensioned to allow passage of the actuator 640 and the needle-enveloping device 630.

Unlike the fourth embodiment 4, however, the needle enveloping device 8 is designed to be attached to a surface of the patient's body. In this respect, the base 610 can have an attaching device that secures the needle device 8 to the surface of the patient's skin for a prolonged period. The attaching device, for instance, can be an adhesive layer 617 provided on an outer surface 616 (FIG. 32) of the base 610. The attaching device can further include a strap, tape, band, or the like (not shown), which allows the patient to additionally secure the device 8 to the surface of a desired body site. Alternatively, the adhesive layer can be placed only on the outer surface of the lower end 635 of the needle shield 631, with the device held with a strap, tape, band, or the like (not shown).

The actuator 640 comprises a depression member 650 and a needle holder 660. The actuator depression member 650 is movably mounted, e.g., up and down, to the housing 620 and biased upwardly relative to the base 610 using compression spring 665 positioned between the needle holder 660 and the depression member 650. The needle holder 660 is movably mounted to the housing between a retracted (unactuated) position (FIG. 32, 33) and an extended (actuated) position (FIG. 34). The compression spring 665 positioned between the depression member 650 and the needle holder 660 biases the needle holder 660 and the depression member 650 in the opposite directions, the needle holder 660 to the actuated position and the depression member 650 upwardly away from the needle holder 660.

The depression member 650 can be formed of a cylindrical hollow body, e.g., a cup-like body, having a closed top end 652 and an open bottom 654. The depression member 650 has at least a pair of outwardly opposing stops 651 at a lower portion thereof. The stops 651 can abut against the upper end of the recesses formed in the housing sleeve 621 to retain the depression member 650 within the housing 620, where the upper surface of the depression member 650 can remain flush with the upper surface of the housing 620. The depression member 650 also can be recessed inside or protruding out of the housing 620 instead of being flush. The stops 651 and the sleeve 621 keep the depression member from moving upwardly beyond the position shown in FIG. 33.

The device 8 further can include a safety tab or lock 670 for locking the depression member 650 in place. Referring to FIG. 32, which more clearly shows the safety tab 670, the safety tab 670 is slidable mounted to the housing 620 adjacent to the depression member 650. The safety tab 670 is movable between a lock position (FIG. 32) and an unlock position (FIG. 34). The safety tab 670 has a lock member 672 in a form of a protrusion insertable into a sidewall opening 653 formed in the depression member 650 to prevent the depression member 650 from moving when the safety tab 670 is in the lock position. The safety tab 670 can be biased toward the lock position, using a spring or the like (not shown), or can include detents or the like, as shown in FIG. 32. The detent can be a projection 674 and complementary recesses 625. In the embodiment shown, the safety tab 670 has the projection 674 and the housing has the complementary pair of recesses 625 at which the projection 674 can rest to provide positive lock and unlock positions. Alternatively, the projection and recesses can be positioned vice-versa.

Referring to FIGS. 32 and 33, the needle holder 660 extends downwardly, concentric with the body depression member 650 and the needle N, which is fixedly attached to the lower end of the needle holder 660. The needle holder 660 can have a passage 661 in which upper end of the needle N protrudes thereinto so that a drug delivery tube or port 662 (communicating with a reservoir (not shown)) can be attached to the upper protruding portion of the needle N. The depression member 650 can have a slot 656 to provide a clearance for the port 662. That is, when the needle holder 650 is in the retracted position, the port 662 can rest in the slot 656. Depressing the depression member 650 after the safety tab is moved to the unlock position allows the needle holder 660 to propel downwardly (from the spring force) so that the needle N can penetrate into the body B, as shown in FIG. 34.

The needle holder 660 is locked in the retracted position (FIG. 32) until the depression member 650 releases it. This locking feature comprises a pair of opposing projections 663 formed on the needle holder. The projections 663 rest on a lock member 680 extending upwardly from the base 610, concentric with its lower opening 624. The lower end of the depression member 650 has diametrically opposing cam surfaces 657 designed to abut against and spread open the lock member 680 to allow passage of the needle holder 660. Specifically, referring to FIGS. 32-33, the lock member 680 comprises a pair of diametrically opposing upstanding legs 682 (see FIGS. 33 and 34) extending upwardly from the base 610, an upper resting surface 683 on each of the legs, and outwardly and upwardly extending portion 684 extending adjacent the upper resting surface 683. Each upstanding leg 682 also has a slot or channel 685 dimensioned to accommodate one of the opposing projections 663. When the depression member 650 is pushed down, the cam surfaces 657 abut against the outwardly and upwardly extending portion 684 and spread apart the upstanding legs 682 sufficient to clear the opposing projections 663. Once the projections 663 clear the resting surfaces 683, the spring 665 urges the needle holder 660 down toward the actuated position (FIG. 34). The slots 685 receive the projections and allow the needle holder 660 to move down to the actuated position. The projections 663 also act as stops to limit the downward movement of the needle N. The projections 663 abut against the base to control the depth of needle penetration. Thus, the device does not apply continuous pressure to the skin. In this embodiment, since the spring 665 propels the needle N into the body B, the needle insertion can be more consistently applied. Moreover, the actuator only needs to move down a relatively short distance, just enough to spread apart the lock member 680. It should be noted that since the spring 665 biases the actuator 640 upwardly, after depression of the same, it returns to its upward position as a result of the spring force.

An electric switch (not shown) can be actuated with the depression member 650 for automatic drug delivery. For instance, a second push on the depression member 650 can activate a switch for automatic drug delivery. In this instance, the user moves the safety tab 670 to the lock position to prevent accidental drug delivery, which can also be prevented using electronic hardware or software. For instance, to activate the drug delivery, the software or hardware can be set so that the user needs to depress the depression member 650 twice, each for a predetermined period.

Figure 36:
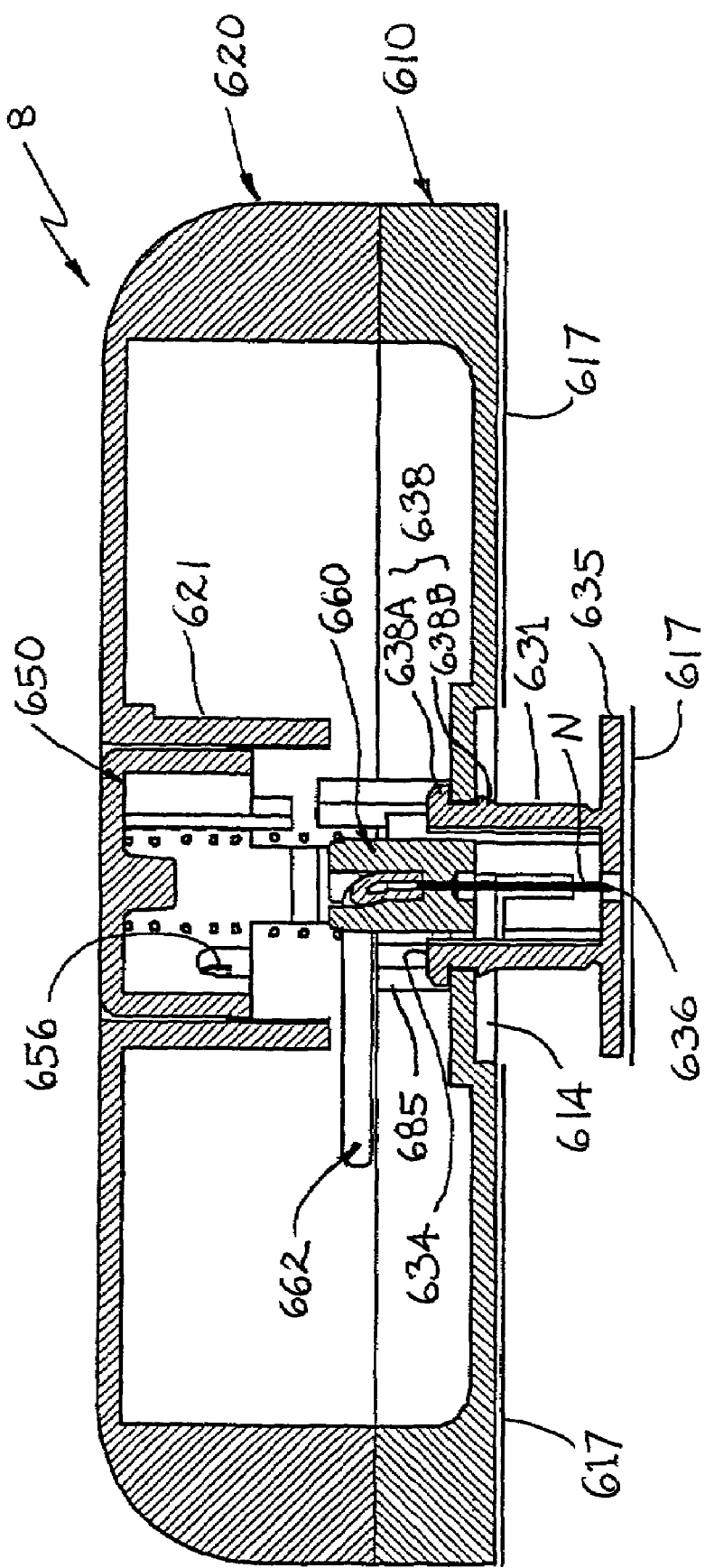
FIG. 36 is a view similar to FIG. 35, but illustrates a different cross-sectional view taken along line 36-36 of FIG. 31.

Referring to FIGS. 35-36, the needle enveloping mechanism 630 comprises a needle shield 631 slidably mounted concentrically between the lock member 680 and the needle holder 660. The needle shield 631 is a substantially hollow body with an open upper end 634 and a closed lower end 635 with an opening 636 to permit passage of the needle N. The needle shield 631 is movable between a retracted position (FIGS. 32-34) and an extended position (FIG. 35-36). In this respect, the needle shield 631 has diametrically opposing slots or channels 637 for accommodating the projections 663, to allow the needle shield 631 to slide relative to the needle holder 660.

In the present embodiment, a portion of the adhesive layer 617 adhered to the lower end 635 of the needle shield remains attached to the skin as the user detaches the device 8 from the skin. See FIG. 33. The adhesive force between the skin and the lower end 635 of the needle shield 631 is greater than the force required to slide or pull out the needle shield 631 from the housing 620. Accordingly, as the user pulls off the device 8, the needle shield 631 remaining adhered to the skin extends outwardly. The adhesive layer 617 can include perforation or the like (not illustrated) to enable the adhesive layer 617 to tear around the lower end 635 of the needle shield, or can be pre-separated around the lower end 635. This allows the remainder of the adhesive layer 617 to peel off the skin easier, while the adhesive layer portion on the lower end 635 remains attached to the skin. Also, as previously mentioned, the adhesive layer 617 can be placed on at the lower end 635 of the needle shield 631, while the device is held to the patient with other fastening means.

When the needle holder 660 is in the retracted position, as shown in FIG. 33, the upper ends 637U of the slots 637 abut against the needle-holder projections 663 to prevent the needle shield 631 from extending outwardly. Only when the needle holder 660 is moved to the actuated position, as shown in FIG. 34, can the needle shield 631 extend outwardly. Moreover, referring to FIG. 35, the upper ends of the slots 637 abut against the needle-holder projections 663 to limit the outward extent.

Referring to FIG. 36, the shield 631 preferably includes a lock 638 that automatically locks the needle shield 631 once it is moved to the extended position (FIG. 35-36). The lock 638 includes first diametrically opposing stops 638A and second diametrically opposing stops 638B that lock the shield 631 in place after it is moved to its extended position, as shown in FIG. 20. The first stops 638A can be formed at the upper end of the shield 631 and can abut against the peripheral edge of the lower opening 624 formed in the base 610 to limit the outward extension. Thus, both the needle-shield projections 663 and the first stops 638A can limit the outward extension. The second stop 638B can be a plurality of one-way latches or detents, such as angled projections or a flange, that allow the shield 631 to slide out, but not in reverse. As the shield 631 is locked in place, the device 8 is rendered inoperative.

In operation of the needle-enveloping device 8, referring to FIGS. 31-36, the needle-enveloping device 8 is positioned so that the base 610 contacts and adheres to the body skin, as shown in FIG. 34. The user first moves the safety tab 670 to the unlock position to unlock the depression member 650. This causes the protrusion 672 to move out of the opening 653 and thus clears the way for downward travel of the depression member 650. The user then presses the depression member 650, which expands or spreads apart the lock member 680 to allow passage of the needle holder 660 into the lock member 680. Once the needle holder 660 is unrestrained from moving downwardly, the spring 665 takes control and immediately propels the needle holder 660 downwardly, sliding relative to the needle shield 631. When the needle N penetrates into the body B, as shown in FIG. 34, the needle N can deliver drug to the user through its port 662. If an electronic delivery system is employed, the user can press the depression member 650 for the second time to activate the automatic drug delivery. The electronic delivery system (not shown) can provide pulsatile or bolus drug delivery. The first push on the depression member 650 for penetrating the needle into the skin surface of the body B can also activate the electronic delivery system, i.e., to start a predetermined or preprogrammed delivery profile (e.g., one pulse per hour). Additionally depressing the depression member 650 can create extra boluses. The user can move the safety tab 670 to the lock position to prevent accidental bolus delivery, and/or deploy software or hardware to prevent unintended drug delivery.

Once the drug delivery is completed, the user then removes the device 8 by peeling the device 8 off the skin. Because the needle shield 631 can freely extend outwardly, the adhesive layer 617 attached to the lower end 635 thereof exerting the pulling force pulls out the shield 631, as shown in FIG. 35, to automatically cover or shroud the needle N. The shield 631 locks into final position to permanently shroud the needle when the tabs 638 sandwich the base 610 therebetween, as shown in FIG. 36. At this point, the device is in condition for safe handling and proper disposal.

Although the present needle device has been described in terms of delivering drug to a person or animal, it should be noted that the present needle device can be used for other purpose, such as delivering fluid to inanimate objects.

Given the disclosure of the present invention, one versed in the art would appreciate that there may be other embodiments and modifications within the scope and spirit of the present invention. For example, while references in the embodiments described springs, it is contemplated that any biasing element, such as an elastic material or other means could be used. Accordingly, all modifications attainable by one versed in the art from the present disclosure within the scope and spirit of the present invention are to be included as further embodiments of the present invention. The scope of the present invention accordingly is to be defined as set forth in the appended claims.

We claim:

1. A needle device comprising:
    a housing having a base for placement against a surface of a needle-penetrating site, the base including a first opening;
    a needle mounted for a movement between a retracted position in the housing and an extended position, a portion of the needle extending through the first opening in the extended position;
    an actuator movably mounted to the housing and movable between a primary unactuated position in which the needle is in the retracted position, an actuated position in which the needle is in the extended position, and a secondary unactuated position in which the needle is in the retracted position; and
    a retraction mechanism, in direct contact with the site surface when the base is placed against the site surface, that automatically moves the actuator to the secondary unactuated position responsive to releasing the base from the site surface, wherein the actuator is not movable between the secondary unactuated position and the actuated position when the base is placed on the site surface.

2. A needle device according to claim 1, wherein the needle is biased toward the retracted position.

3. A needle device according to claim 2, wherein the retraction mechanism permanently locks the needle in the retracted position after releasing the base from the site surface.

4. A needle device according to claim 1, wherein the retraction mechanism includes a trigger member movably mounted to the housing, the trigger member having a first portion adapted to engage the actuator and a second portion adapted to contact the site surface.

5. A needle device according to claim 4, wherein the trigger member is pivotally mounted to the housing.

6. A needle device according to claim 5, wherein the base further includes a second opening through which the second portion of the trigger member is adapted to contact the site surface.

7. A needle device according to claim 4, wherein the housing has an actuator guide that guides the actuator through a predetermined path of movement.

8. A needle device according to claim 7, wherein the guide comprises a substantially U-shaped channel formed in the housing, the U-shaped channel comprising a first substantially vertical guide portion, a second substantially vertical guide portion and a horizontal guide portion connecting lower ends of the first and second vertical portions.

9. A needle device according to claim 8, wherein the actuator is rotatably and vertically movably mounted to the housing, and further includes a pin adapted to be guided in the U-shaped channel.

10. A needle device according to claim 9, further including a spring that biases the actuator to the secondary unactuated position the spring having one end thereof fixedly mounted to the actuator and another end thereof fixedly mounted to the base to enable creation of a spring torsional load when the actuator is rotated relative to the base.

11. A needle device according to claim 10, wherein the spring is torsionally preloaded to rotate the actuator from the first vertical guide portion to the second vertical guide portion through the horizontal guide portion upon moving the actuator to the actuated position.

12. A needle device according to claim 11, wherein the trigger member is pivotally mounted to the housing and the first portion of the trigger member is adapted to engage the pin and prevent the actuator from moving to the second unactuated position when the pin is positioned in the second vertical guide portion and the second portion thereof is contacting the site surface.

13. A needle device according to claim 12, wherein the base further includes a second opening through which the second portion of the trigger member is adapted to contact the site surface.

14. A needle device according to claim 13, wherein the actuator guide further includes a lock portion contiguous with the second vertical guide portion.

15. A needle device according to claim 14, wherein the spring torsional preloading further rotates the actuator into the lock portion to lock the actuator from moving to the actuated position.

16. A needle device comprising:
a housing having a base adapted to be placed next to a surface of a needle-penetrating site, the base including at least a first opening and a second opening;
a needle mounted for a movement between a retracted position in the housing and an extended position, where a portion of the needle extends through the first opening when in the extended position;
an actuator movably mounted to the housing and movable between an unactuated position at which the needle is in the retracted position and an actuated position at which the needle is in the extended position, the actuator being biased toward the unactuated position;
a retraction mechanism responsive to contact with the site surface through the second opening, wherein when the base is placed next to a site surface and the needle is moved to the extended position the retraction mechanism locks the needle in the extended position until the base is released from next to the surface whereby the retraction mechanism automatically moves the needle from the extended position to the retracted position.

17. A needle device according to claim 16, further comprising a locking mechanism that prevents the needle from moving back to the extended position once the needle has been moved from the extended position to the retracted position.

18. A needle device according to claim 17, wherein the locking mechanism is integral with the retraction mechanism.

19. A needle device according to claim 16, wherein the retraction mechanism includes a cover member for covering the opening after a tip of the needle moves from the extended position to the retracted position, in which the tip of the needle is received within the housing.

\* \* \* \* \*